(12) United States Patent
Schoenle et al.

(10) Patent No.: US 10,335,042 B2
(45) Date of Patent: Jul. 2, 2019

(54) METHODS, DEVICES AND SYSTEMS FOR SENSING, MEASURING AND/OR CHARACTERIZING VESSEL AND/OR LESION COMPLIANCE AND/OR ELASTANCE CHANGES DURING VASCULAR PROCEDURES

(71) Applicant: Cardiovascular Systems, Inc., New Brighton, MN (US)

(72) Inventors: Victor L. Schoenle, Greenfield, MN (US); Thomas B. Hoegh, Edina, MN (US); Bruce J. Persson, Shoreview, MN (US); Kayla Eichers, Minneapolis, MN (US); Matthew Tilstra, Rogers, MN (US); Richard C. Mattison, Zimmerman, MN (US); Joseph P. Higgins, Minnetonka, MN (US); Michael J. Grace, Brooklyn Park, MN (US); Matthew Saterbak, Robbinsdale, MN (US); Matthew D. Cambronne, St. Anthony, MN (US); Robert E. Kohler, Lake Elmo, MN (US)

(73) Assignee: Cardiovascular Systems, Inc., New Brighton, MN (US)

( * ) Notice: Subject to any disclaimer, the term of this patent is extended or adjusted under 35 U.S.C. 154(b) by 0 days.

(21) Appl. No.: 14/801,269

(22) Filed: Jul. 16, 2015

(65) Prior Publication Data

US 2016/0183807 A1 Jun. 30, 2016

Related U.S. Application Data

(63) Continuation-in-part of application No. 14/315,774, filed on Jun. 26, 2014.

(Continued)

(51) Int. Cl.
 *A61B 5/05* (2006.01)
 *A61B 5/02* (2006.01)
 (Continued)

(52) U.S. Cl.
 CPC ........ *A61B 5/02007* (2013.01); *A61B 5/0066* (2013.01); *A61B 5/02152* (2013.01);
 (Continued)

(58) Field of Classification Search
 None
 See application file for complete search history.

(56) References Cited

U.S. PATENT DOCUMENTS

| 3,000,197 A | 9/1961 | Ruegg et al. |
| 3,177,684 A | 4/1965 | Bossler, Jr. |

(Continued)

FOREIGN PATENT DOCUMENTS

| WO | WO1999/34724 | 7/1999 |
| WO | WO2012/166332 | 12/2012 |
| WO | WO2014/210450 | 12/2014 |

OTHER PUBLICATIONS

International Search Report and Written Opinion issued in related PCT application No. PCT/US16/28541, dated Sep. 14, 2016.

(Continued)

*Primary Examiner* — Patricia Mallari
*Assistant Examiner* — Jairo H Portillo
(74) *Attorney, Agent, or Firm* — Barnes & Thornburg LLP; Jeffrey R. Stone

(57) ABSTRACT

The present system is directed in various embodiments to methods, devices and systems for sensing, measuring and evaluating compliance in a bodily conduit. In other embodiments, the methods, devices and systems sense, measure, determine, display and/or interpret compliance in a bodily conduit and/or a lesion within the bodily conduit. In all (Continued)

embodiments, the sensing, measuring, determining, displaying and/or interpreting may occur before, during and/or after a procedure performed within the bodily conduit. An exemplary conduit comprises a blood vessel and an exemplary procedure comprises a vascular procedure such as atherectomy, angioplasty, stent placement and/or biovascular scaffolding.

17 Claims, 23 Drawing Sheets

Related U.S. Application Data

(60) Provisional application No. 62/026,288, filed on Jul. 18, 2014, provisional application No. 62/040,598, filed on Aug. 22, 2014, provisional application No. 62/061,883, filed on Oct. 9, 2014, provisional application No. 62/119,635, filed on Feb. 23, 2015, provisional application No. 61/871,529, filed on Aug. 29, 2013, provisional application No. 61/840,693, filed on Jun. 28, 2013.

(51) Int. Cl.
*A61B 5/0215* (2006.01)
*A61B 5/107* (2006.01)
*A61B 5/00* (2006.01)
*A61B 8/12* (2006.01)
*G16H 50/20* (2018.01)
*G06F 19/00* (2018.01)
*A61B 17/00* (2006.01)
*A61B 90/00* (2016.01)
*A61B 5/06* (2006.01)
*A61B 34/20* (2016.01)

(52) U.S. Cl.
CPC .......... *A61B 5/1076* (2013.01); *A61B 5/6853* (2013.01); *A61B 8/12* (2013.01); *G16H 50/20* (2018.01); *A61B 5/062* (2013.01); *A61B 2017/00022* (2013.01); *A61B 2034/2051* (2016.02); *A61B 2090/065* (2016.02); *G06F 19/3481* (2013.01)

(56) References Cited

U.S. PATENT DOCUMENTS

| | | | |
|---|---|---|---|
| 3,661,148 | A | 5/1972 | Kolin |
| 4,651,738 | A | 3/1987 | Demer et al. |
| 4,932,419 | A | 6/1990 | de Toledo |
| 4,951,677 | A | 8/1990 | Crowley et al. |
| 5,052,404 | A | 10/1991 | Hodgson |
| 5,084,060 | A | 1/1992 | Freund et al. |
| 5,103,543 | A | 4/1992 | Hodgson |
| 5,115,814 | A | 5/1992 | Griffith et al. |
| 5,171,299 | A | 12/1992 | Heitzmann et al. |
| 5,275,169 | A | 1/1994 | Afromowitz et al. |
| 5,297,556 | A | 3/1994 | Shankar |
| 5,314,438 | A | 5/1994 | Shturman |
| 5,343,867 | A | 9/1994 | Shankar |
| 5,373,619 | A | 12/1994 | Fleischhacker et al. |
| 5,423,323 | A | 6/1995 | Orth |
| 5,437,282 | A | 8/1995 | Koger et al. |
| 5,438,997 | A | 8/1995 | Sieben et al. |
| 5,464,407 | A | 11/1995 | McGuire |
| 5,522,875 | A | 6/1996 | Gates et al. |
| 5,533,969 | A | 7/1996 | Mulder |
| 5,540,707 | A | 7/1996 | Ressemann et al. |
| 5,562,275 | A | 10/1996 | Weissenfluh et al. |
| 5,678,296 | A | 10/1997 | Fleischhacker et al. |
| 5,752,522 | A | 5/1998 | Murphy |
| 5,771,895 | A | 6/1998 | Slager |
| 5,803,812 | A | 9/1998 | Kakiuchi et al. |
| 5,816,923 | A | 10/1998 | Milo et al. |
| 5,836,868 | A | 11/1998 | Ressemann et al. |
| 5,865,801 | A | 2/1999 | Houser |
| 5,891,089 | A | 4/1999 | Katz et al. |
| 5,932,035 | A | 8/1999 | Koger et al. |
| 5,992,419 | A | 11/1999 | Sterzer et al. |
| 6,010,511 | A | 1/2000 | Murphy |
| 6,179,858 | B1 | 1/2001 | Squire et al. |
| 6,217,595 | B1 | 4/2001 | Shturman et al. |
| 6,280,332 | B1 | 8/2001 | Knutson |
| 6,354,999 | B1 | 3/2002 | Dgany et al. |
| 6,494,890 | B1 | 12/2002 | Shturman et al. |
| 6,616,597 | B2 | 9/2003 | Schock et al. |
| 6,626,853 | B2 | 9/2003 | White et al. |
| 6,669,662 | B1 | 12/2003 | Webler |
| 6,685,696 | B2 | 2/2004 | Fleischhacker et al. |
| 6,793,634 | B2 | 9/2004 | White et al. |
| 6,818,001 | B2 | 11/2004 | Wulfman et al. |
| 6,935,999 | B2 | 8/2005 | Schock et al. |
| 7,037,271 | B2 | 5/2006 | Crowley |
| 7,077,812 | B2 | 7/2006 | Naghavi |
| 7,112,170 | B2 | 9/2006 | Schock et al. |
| 7,229,403 | B2 | 6/2007 | Schock et al. |
| 7,454,244 | B2 | 11/2008 | Kassab et al. |
| 7,479,120 | B2 | 1/2009 | Gregersen |
| 7,753,852 | B2 | 7/2010 | Maschke |
| 7,947,001 | B1 | 5/2011 | Sarvazyan |
| 7,967,757 | B2 | 6/2011 | Roteliuk |
| 8,043,314 | B2 | 10/2011 | Noriega et al. |
| 8,208,990 | B2 | 6/2012 | Maschke |
| 8,353,922 | B2 | 1/2013 | Noriega et al. |
| 8,465,452 | B2 | 6/2013 | Kassab |
| 8,646,325 | B2 | 2/2014 | Hoem et al. |
| 2002/0103430 | A1* | 8/2002 | Hastings ............... A61B 5/055 600/411 |
| 2003/0092977 | A1 | 5/2003 | Sahatjian |
| 2003/0139689 | A1 | 7/2003 | Shturman et al. |
| 2003/0167010 | A1 | 9/2003 | Pinsky |
| 2004/0102722 | A1 | 5/2004 | Naghavi |
| 2005/0249391 | A1 | 11/2005 | Kimmel et al. |
| 2006/0052700 | A1* | 3/2006 | Svanerudh ........... A61B 5/0215 600/438 |
| 2006/0058592 | A1 | 3/2006 | Bouma et al. |
| 2006/0106321 | A1 | 5/2006 | Lewinsky et al. |
| 2007/0083126 | A1 | 4/2007 | Marko et al. |
| 2007/0232933 | A1 | 10/2007 | Gille et al. |
| 2008/0027358 | A1 | 1/2008 | Gregersen et al. |
| 2008/0161730 | A1 | 7/2008 | McMahon et al. |
| 2008/0221601 | A1 | 9/2008 | Huynh et al. |
| 2009/0195514 | A1 | 8/2009 | Glynn et al. |
| 2009/0216133 | A1 | 8/2009 | Kassab |
| 2009/0284332 | A1 | 11/2009 | Moore et al. |
| 2011/0152907 | A1 | 6/2011 | Escudero et al. |
| 2011/0295107 | A1 | 12/2011 | Kargar et al. |
| 2012/0029282 | A1 | 2/2012 | Yamakawa et al. |
| 2012/0109170 | A1* | 5/2012 | Shturman ...... A61B 17/320758 606/159 |
| 2012/0116237 | A1* | 5/2012 | Harks ................. A61B 5/1107 600/508 |
| 2012/0165702 | A1 | 6/2012 | Hauck |
| 2012/0172656 | A1 | 7/2012 | Walters et al. |
| 2012/0245457 | A1 | 9/2012 | Crowley |
| 2012/0265002 | A1 | 10/2012 | Roehn et al. |
| 2012/0265062 | A1 | 10/2012 | Sliwa et al. |
| 2012/0029283 | A1 | 12/2012 | Yamakawa et al. |
| 2013/0090679 | A1 | 4/2013 | Hoem et al. |
| 2013/0131650 | A1* | 5/2013 | Whitman ........... A61B 10/0233 606/1 |
| 2013/0165908 | A1 | 6/2013 | Purdy et al. |

(56) References Cited

U.S. PATENT DOCUMENTS

2013/0303914 A1* 11/2013 Hiltner .................. A61B 8/12
600/449
2015/0080747 A1   3/2015 Schoenle

OTHER PUBLICATIONS

International Preliminary Report on Patentability for PCT Application No. PCT/US2015/040838, filed Jul. 17, 2015, dated Feb. 2, 2017.
International Preliminary Report on Patentability, dated Jan. 16, 2018 for PCT Application No. PCT/US2016/028541, filed Jul. 16, 2015.

* cited by examiner

MC CROWN ORBIT/POSITION EQN.

1. $\Delta x_1 = \frac{-x_1}{2}\left(\frac{\Delta - B_1}{B_1}\right)$

ADD SECOND MC SENSOR, S2

2. $\Delta x_2 = \frac{-x_2}{2}\left(\frac{\Delta - B_2}{B_2}\right)$

TWO ADDITIONAL KNOWNS

3. $x_T = x_1 + x_2$
4. $\Delta x_1 = -\Delta x_2$

MC ORBIT DIAMETER

5. $\Delta x_1 = \dfrac{\frac{1}{2}x_T}{\left[\dfrac{B_2}{\Delta - B_2} - \dfrac{B_1}{\Delta - B_1}\right]}$

- DON'T NEED TO KNOW x1 OR x2

MC ABS. POS. <u>DURING MOVEMENT</u>

6. $x_1 = x_T \cdot \left[1 - \left(\dfrac{\Delta B_2}{B_2}\right) \cdot \left(\dfrac{B_1}{\Delta B_1}\right)\right]$

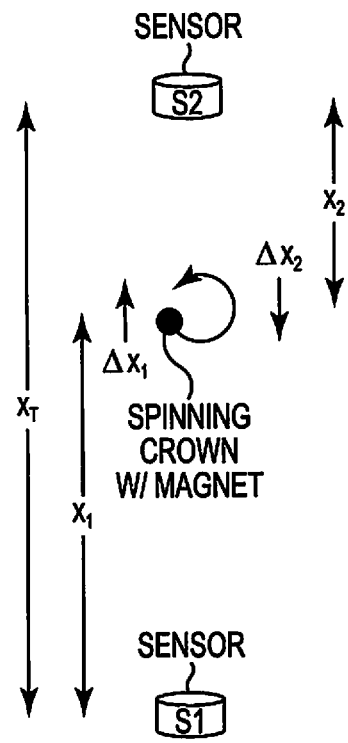

Fig. 27

METHODS, DEVICES AND SYSTEMS FOR SENSING, MEASURING AND/OR CHARACTERIZING VESSEL AND/OR LESION COMPLIANCE AND/OR ELASTANCE CHANGES DURING VASCULAR PROCEDURES

CROSS-REFERENCE TO RELATED APPLICATIONS

This application is a continuation-in-part of application Ser. No. 14/315,774, entitled "Devices, Systems and Methods for Locally Measuring Biological Conduit and/or Lesion Compliance, Opposition Force and Inner Diameter of a Biological Conduit", filed Jun. 26, 2014 and further claims priority to App. Ser. No. 62/026,288, entitled "Magnetic Carrier Wave Sensor and RF Emitter and Sensor in Atherectomy Procedures", filed Jul. 18, 2014, and to App. Ser. No. 62/040,598, entitled "Devices, Systems and Methods for Performing Vascular Procedure(s) with Integrated Fractional Flow Reserve", filed Aug. 22, 2014, and to App. Ser. No. 62/061,883, entitled "Devices, Systems and Methods for Performing Vascular Procedures with Integrated Intravascular Ultrasound Lesion and Vessel Compliance Measurement", filed Oct. 9, 2014, and to App. Ser. No. 62/119,635, entitled "Magnetic Carrier—Chord Method", filed Feb. 23, 2015, the entire contents of each of which are hereby incorporated by reference.

FIELD OF THE INVENTION

The present invention generally relates to visualizing a lesion within a vessel, characterizing lesion composition, measuring vessel diameter, and/or sensing, measuring and characterizing a vessel and/or lesion compliance and/or elastance change during a vascular procedure.

DESCRIPTION OF THE RELATED ART

A variety of techniques and instruments have been developed for use in the removal or repair of tissue in arteries and similar body passageways, e.g., biological conduits. A frequent objective of such techniques and instruments is the removal of atherosclerotic plaques in a patient's arteries. Atherosclerosis is characterized by the buildup of fatty deposits (atheromas) in the intimal layer (under the endothelium) of a patient's blood vessels. Very often over time, what initially is deposited as relatively soft, cholesterol-rich atheromatous material hardens into a calcified atherosclerotic plaque. Such atheromas restrict the flow of blood, and therefore often are referred to as stenotic lesions or stenoses, the blocking material being referred to as stenotic material. If left untreated, such stenoses can cause angina, hypertension, myocardial infarction, strokes and the like.

Characterization of the compliance and/or elastance of the subject biological conduit, e.g., blood vessel, as well as the compliance and/or elastance of a lesion within the conduit, e.g., blood vessel, is a critical element during vascular procedures such as, without limitation, atherectomy (rotational or other atherectomy processes), ablation, angioplasty, stent placement or biovascular scaffolding.

Imaging of the subject conduit using, e.g., intravascular ultrasound (IVUS) or optical coherence tomography (OCT) techniques are known. IVUS may involve inserting a manipulatable IVUS device, e.g., a catheter or guidewire, carrying one or more ultrasound transducers, to visualize and assess the conduit and lesion, if present, therein. The IVUS imaging process may occur before, during and/or after the particular vascular procedure. Further information regarding IVUS imaging may be found by reference to U.S. Pat. No. 5,771,895; U.S. Pub. 2005/0249391; U.S. Pub. 2009/0195514; U.S. Pub. 2007/0232933; and U.S. Pub. 2009/0284332, the contents of each of which are hereby incorporated by reference in their entirety. The IVUS ultrasound transducer(s) may be mounted on a guidewire, catheter and/or other manipulateable insertable intravascular tool to enable visualizing the conduit, the lesion (when present), evaluation of the diameter of the conduit as well as provide information for assessing the type and/or composition of the lesion as well as the progress of a vascular procedure, including information concerning the completeness of the procedure. Such imaging data may be used in combination with other data such as functional data.

Functional data regarding the conduit and/or lesion therein may also be obtained using known techniques. For example, it is known to measure a pressure drop-velocity relationship such as Fractional Flow Reserve (FFR) or Coronary Flow Reserve (CFR) to obtain information about conduit condition and degree of occlusion due to the lesion or other occlusive media. FFR measurements, e.g., may be obtained using pressure sensors mounted on a guide wire as is known in the art. Thus, pressure measurements may be taken proximal to the area of interest within the conduit, e.g., and without limitation proximal the lesion, and distal to the area of interest, e.g., the lesion, to determine severity and status of vascular procedure being employed.

Further, functional data may be obtained within the subject conduit and/or lesion therein, using inflatable devices, e.g., balloons. Known inflatable devices having pressure sensors incorporated thereon, with manual measurement and control of the pressure levels and inflation rate. In some cases, a syringe and associated pressure gauge is used to inflate and/or deflate the inflatable device. In the known solutions, a balloon inflation device is a hand-held device comprising a screw-driven syringe with a pressure gauge that indicates the inflation pressure than the balloon is under during operation. The operator may manually rotate the screw to the desired inflation pressure. The operator must then visually estimate how well the device is contacting the wall of the vessel and to match the device to the vessel, e.g., artery. Each time the operator requires a visualization of the vessel to device conformation, the patient must be injected with a contrast fluid with subsequent production of an x-ray film to enable the visualization. The visualization process is undesirable as it is time consuming and requires harmful drugs and x-rays.

None of these known systems or measurement processes are capable of accurately measuring a conduit's compliance or elastance.

Vessel compliance and elastance are significant physiological parameters. For compliance, an increase in volume occurs in a vessel when the pressure in that vessel is increased. The tendency of the arteries and veins to stretch in response to pressure has a large effect on perfusion and blood pressure. This physically means that blood vessels with a higher compliance deform easier than lower compliance blood vessels in response to a change of pressure or volume conditions.

Compliance is the ability of a biological conduit, e.g., a blood vessel, to distend and increase volume with increasing transmural pressure or the tendency of a biological conduit, e.g., a blood vessel, to resist recoil toward its original dimensions on application of a distending or compressing force. It is the reciprocal of "elastance". Hence, elastance is a measure of the tendency of a biological conduit, e.g., blood vessel, to recoil toward its original dimensions upon removal of a distending or compressing force.

The compliance characteristics of healthy vessels depend on two factors: (1) initial vessel shape; and (2) vessel components that include vascular smooth muscle, collagen, elastin and other interstitial elements. Volume and pressure relationship is non-linear which, in turn, means that there is no single parameter that may be used to present vessel compliance.

Systemic arterial stiffness, e.g., is the overall opposition of the exemplary arteries due to pulsatile effects of the ventricular ejection. The pressure curve is used to estimate the stiffness. Regional assessment of arterial stiffness is done at arterial regions which have physiologic importance, such as aorta epicedial vessels and limbs. Local assessment of stiffness is measured at reflected wall stiffness.

Thus, compliance for a conduit, e.g., vessels, is the ability to defotin under an applied pressure. Physically, it is the inverse of stiffness. Thus, compliance may be expressed as the change of one or more of the area, diameter or volume of the lumen under consideration divided by the change in internal pressure, or forces, acting on the lumen. The compliance during the cardiac cycle is the change in cross-sectional area for a unit length of the vessel and the change in arterial pressure which is typically quantified as the difference between the systolic and diastolic pressures. Thus, compliance is the slope of the volume-pressure curve at a given pressure. Stated differently, compliance is the slope of a tangent to the volume-pressure curve. Normalized compliance is obtained by dividing compliance (change in volume (or area)/change in pressure) by the conduit, e.g., vessel, diameter to eliminate the effects of vessel size.

The volume-pressure relationship (i.e., compliance) for an artery and vein are highly significant in determining not only the severity of occlusion, but also, inter alia, the composition and/or type of the lesion when present, assessment of the progress of a vascular procedure, e.g., atherectomy, and determination of the reaching of the endpoint or conclusion of a vascular procedure such as atherectomy. It is known that compliance decreases at higher pressures and volumes (i.e., vessels become "stiffer" at higher pressures and volumes).

Despite the known capabilities in these areas, unmet needs still exist in the quantifying of a subject conduit's compliance, or the compliance of a lesion within the conduit, e.g., blood vessel, at a specific location, e.g., the site of an occlusion. It is, for example, necessary to know the compliance of a conduit and/or lesion, before, during and/or after a vascular procedure.

BRIEF SUMMARY OF THE INVENTION

The present system is directed in various embodiments to methods, devices and systems for sensing, measuring and evaluating compliance in a bodily conduit. In other embodiments, the methods, devices and systems sense, measure, determine, display and/or interpret compliance in a bodily conduit and/or a lesion within the bodily conduit. In all embodiments, the sensing, measuring, determining, displaying and/or interpreting may occur before, during and/or after a procedure performed within the bodily conduit. An exemplary conduit comprises a blood vessel and an exemplary procedure comprises a vascular procedure such as atherectomy, angioplasty, stent placement and/or biovascular scaffolding.

BRIEF DESCRIPTION OF THE DRAWINGS

FIG. 27 illustrates graphically and mathematically one embodiment of the present invention for handling movement artifacts.

DETAILED DESCRIPTION

Figure 1:
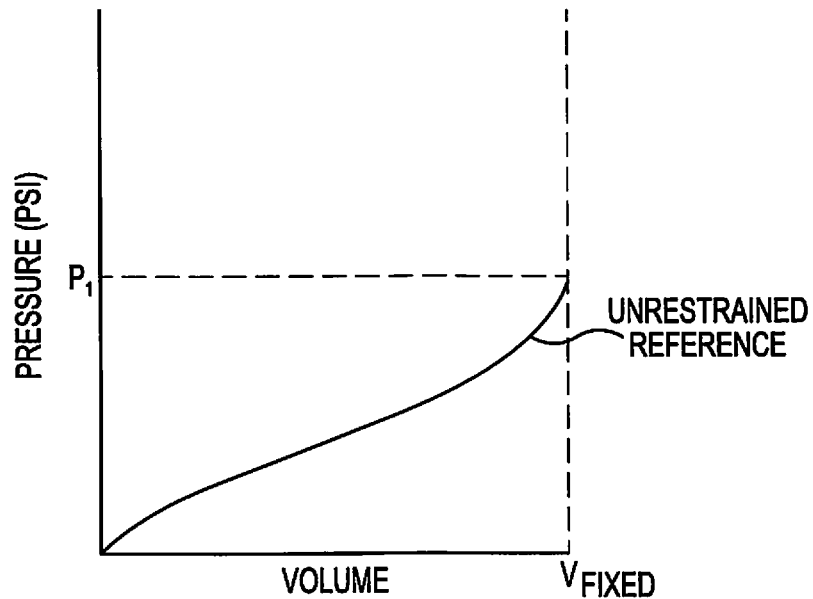
FIG. 1 illustrates a reference inflation compliance curve for an unrestrained balloon with a fixed inflation volume and fixed inflation rate (unrestrained reference)

While the invention is amenable to various modifications and alternative forms, specifics thereof are shown by way of example in the drawings and described in detail herein. It should be understood, however, that the intention is not to limit the invention to the particular embodiments described. On the contrary, the intention is to cover all modifications, equivalents, and alternatives falling within the spirit and scope of the invention.

The present system is directed in various embodiments to methods, devices and systems for sensing, measuring, determining, displaying and/or interpreting compliance of a biological conduit before, during and/or after the performance of a vascular procedure such as atherectomy, including without limitation, rotational atherectomy, ablation, angioplasty, stent placement and/or biovascular scaffolding.

In various embodiments, the present invention is further directed to methods, devices and systems for sensing, measuring, determining, displaying and interpreting compliance of a biological conduit and/or a lesion within the biological conduit before, during and/or after the performance of a vascular procedure such as atherectomy, including without limitation, rotational atherectomy, ablation, angioplasty, stent placement and/or biovascular scaffolding.

An exemplary biological conduit may comprise a blood vessel such as an artery and an exemplary vascular procedure may comprise rotational atherectomy.

FIG. 1 illustrates the development of an unrestrained reference compliance curve using an unrestrained balloon and a fixed inflation volume with a fixed inflation rate. Thus, the pressure measured by a transducer that is operationally attached to the balloon and as will be discussed later is recorded and graphed on the y-axis, while the volume added to the balloon during the inflation process is recorded and graphed on the x-axis. The total volume is fixed (V-Fixed) as is the inflation rate. This process is completed without any restrictive forces on the balloon such as a vessel wall during the inflation process.

The result is a reference compliance inflation curve for a particular balloon, or a balloon having a particular set of characteristics, e.g., size, shape, elasticity. Because the balloon is unrestrained and both the volume and the inflation rate are fixed, it is possible to measure, and record, the outer diameter (OD) of the balloon throughout the inflation process, i.e., the OD of the unrestrained balloon at any point in the inflation process can be mapped to a particular set of pressure, volume coordinate data. The OD data is recorded along with the pressure and volume data for future reference. The OD data may be used to quantify the internal diameter of any biological conduit, e.g., a blood vessel, that the balloon is expanded within as further described below.

Figure 2:
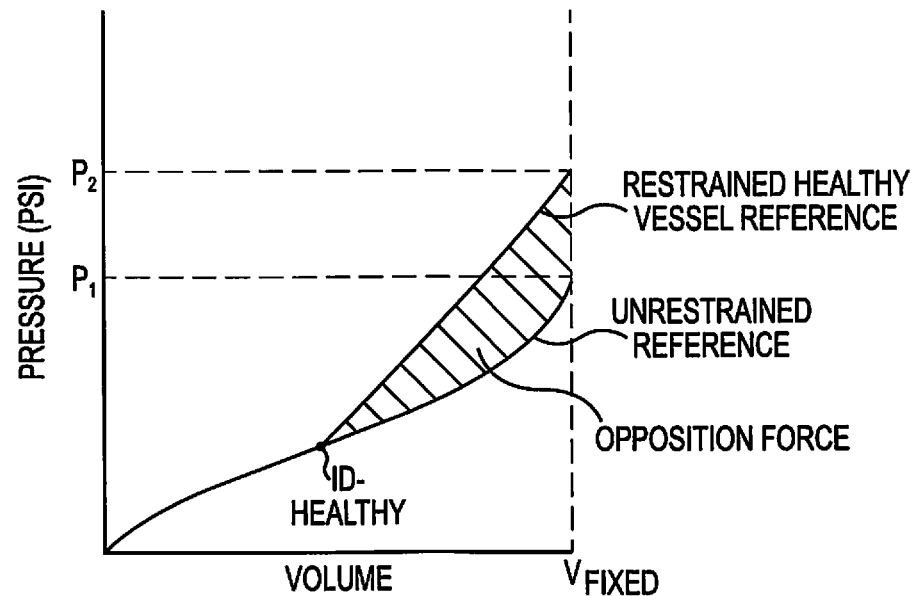
FIG. 2 illustrates the differences between the reference compliance curve of FIG. 1 and an inflation compliance curve from the same balloon with same fixed inflation volume and inflation rate under restrained conditions within a healthy biological conduit, e.g., a blood vessel without a lesion, (restrained reference)

FIG. 2 illustrates the development of a restrained healthy biological conduit, e.g., blood vessel, reference compliance inflation curve using a balloon with the same physical characteristics as that used to develop the unrestrained balloon compliance curve of FIG. 1 as well as the same fixed volume and inflation rate used for the unrestrained reference compliance curve of FIG. 1. The remaining disclosure refers to the subset of blood vessels within the broader category biological conduit which is broadly defined herein as a channel with boundaries or walls within a mammal. This reference is solely for ease of disclosure and not intended to limit the disclosure to blood vessels in any way. The restrained healthy vessel reference compliance curve information relating to the pressure measured by the operationally attached pressure transducer is captured, recorded and graphed against the fixed volume that is infused into the restrained balloon at a fixed inflation rate.

FIG. 2 also comprises unrestrained reference compliance curve data for the same balloon, or one with the same physical characteristics, and for the same fixed volume and inflation rate as used for the restrained reference compliance curve data generation.

Several significant features appear on FIG. 2. First, as the fixed volume is reached, it is clear that the pressure measured within the unrestrained reference at P1, is lower than the pressure measured within the restrained reference at P2. This is the effect of restraint on the inflation. Similarly, the volume changes at a given pressure may also be monitored.

Additionally, following the data from the origin, a point of divergence is reached, where the restrained reference begins to experience higher pressure than the unrestrained reference. This point of divergence is marked on FIG. 2 as ID-Healthy and represents the expansion point at which the restrained balloon encounters resistance in the form of the healthy vessel wall it is expanding within. Stated differently, the expanding balloon first experiences an opposition force at ID-Healthy as a consequence of the expanding balloon encountering the inner diameter of the healthy vessel wall. Consequently, it is now possible to determine the internal diameter of the vessel at the location of the expanding balloon, by comparing the compliance curve of FIG. 2 with the unrestrained reference compliance curve of FIG. 1 and locating the point of divergence marked as ID-Healthy. Next, reference may be made to the previously mapped set of OD's corresponding to a given volume and pressure along the unrestrained reference compliance curve of FIG. 1 and as described above to determine the outer diameter of the restrained healthy vessel reference balloon at ID-Healthy. The outer diameter of the restrained healthy vessel reference balloon at ID-Healthy is the same as the inner diameter of the healthy vessel wall.

Further, the present invention is enabled to measure a quantity defined herein as opposition force, i.e., the force applied by the vessel wall against the expanding balloon, a force not experienced by the unrestrained reference balloon of FIG. 1. This is illustrated graphically by the shaded area in FIG. 2 between the restrained reference compliance curve and the unrestrained reference compliance curve after the point of divergence ID-Healthy discussed above. The opposition "force" quantity may be calculated as a surrogate to force through use of the pressure values. For example, in FIG. 2, at V-Fixed, the opposition force may be characterized as delta P or P2–P1. This calculation may be made at any point in the inflation process for any given volume. Alternatively, the pressures at any given volume within the inflation process may be converted to actual force by dividing the pressure for the restrained and unrestrained reference compliance curves at any point beyond the point of divergence by the surface area of the inflating balloon, a known and/or measurable quantity, and computing the difference between restrained reference force and unrestrained reference force. Still more alternatively, the area between the restrained reference compliance curve and the unrestrained reference compliance curve beyond the point of divergence may be calculated using known mathematical techniques in order to calculate the total opposition force.

Moreover, it is possible to measure the elasticity, or compliance, of the restrained reference compliance curve vessel, based on the slope of the restrained reference compliance curve, i.e., the change in pressure compared with the change in volume, as compared with the slope of the unrestrained reference compliance curve, beginning at the point where the pressure within that restrained reference vessel reaches the point of divergence ID-Healthy discussed above. The steeper the slope of the restrained reference compliance curve as compared with the unrestrained reference compliance curve, the less elastic or compliant is the restraining vessel that the restrained reference balloon is expanding within. In contrast, a slope that is less steep for the restrained compliance curve as compared with the unrestrained reference compliance curve indicates a more compliant, or elastic, vessel. Note that in this case, the restrained reference vessel is healthy and, therefore, the compliance measurement is only for the vessel and not a lesion therein. Compliance, or elasticity, may be measured and/or quantified by comparing the volume changes at given pressures. Alternatively, compliance or elasticity may be quantified by comparing the pressure changes at given volumes. Either of these methods may be evaluated using a slope comparison.

Note further that the restrained healthy vessel reference compliance curve may be generated within a patient in the same vessel that is occluded, but in a relatively healthy section. Alternatively, another similar vessel within the patient may be used to generate the reference data. Still more alternatively, laboratory measurements may be conducted using sleeves of known elasticity in order to build a reference library of incremental volumes, infusion rates and matching those variables in a test matrix against sleeves of incremental elasticity. Herein, elasticity is defined as compliance and the two terms may be used interchangeably. Generally, elasticity, or compliance, is the ability of the vessel, or sleeve, to accommodate, i.e., increase in inner diameter, with an increasing volume and resulting increase in pressure. Note that the increase in diameter and volume are surrogates for area. Consequently, compliance may be expressed as the change in area over the change in pressure. All of these reference library data may be stored in a database that is accessible for comparison purposes during an actual working procedure such as an atherectomy procedure, stent delivery or transcatheter aortic valve replacement (TAVR), and the like to enable the operator to determine real-time progress and sufficiency of the procedure for inner diameter changes, opposition force changes and/or compliance, i.e., elasticity, of the subject biological conduit. In short, the present invention may be used alone or in combination with any procedure that desires data on a conduit's inner diameter and changes thereof, opposition force changes and compliance of the conduit and/or lesion when present.

It is known that a healthy artery, e.g., has an approximate 5 to 7% compliance, or elasticity, when subjected to approximately 100 mm of pressure. This is generally the range required by a healthy artery to accommodate pressure and volume changes at the extremes of physical exertion, i.e., from sleeping to rigorous exercise. Thus, vessels with healthy compliance will experience changes in the inner diameter during increases in pressure and/or volume. Consequently, increases in volume are mitigated in terms of increasing pressure as the flow volume is also increased due to the larger channel. In contrast, vessels lacking healthy compliance will resist changes in inner diameter accommodation in response to increases in pressure and/or volume. Consequently, unhealthy vessels may retain a static diameter during changes in volume which drives pressures to potentially unhealthy levels.

Vessels having occlusions may exhibit these non-compliant properties, in addition to having inner diameters that are smaller than normal due to the occlusive material. Procedures to remove the occlusion, e.g., rotational and/or orbital atherectomy, may be employed to increase the inner diameter of the vessel at the previously partially or completely occluded location as well as to remove the material bound to the inner wall of the vessel which may contribute to a loss of compliance or elasticity.

Further, in some cases, an unrestrained reference compliance curve(s) may be used for analytical comparison against test data without additional use of a restrained healthy vessel reference compliance curve(s). In other cases, a restrained reference compliance curve(s) may be used for analytical comparison against test data without additional use of an unrestrained compliance curve(s). In still other cases, both an unrestrained reference compliance curve and a restrained healthy vessel reference compliance curve may be used to compare against test data. The reference compliance curve data, whether restrained or unrestrained, may be tabulated and stored in a database and/or in the memory of an external device such as a programmable computer or similar device. This data may thus be accessed for comparative purposes as will be discussed herein. In all cases, the present invention may be used to quantify compliance of the biological conduit, e.g., a blood vessel, and/or a lesion that is within the conduit.

Figure 3:
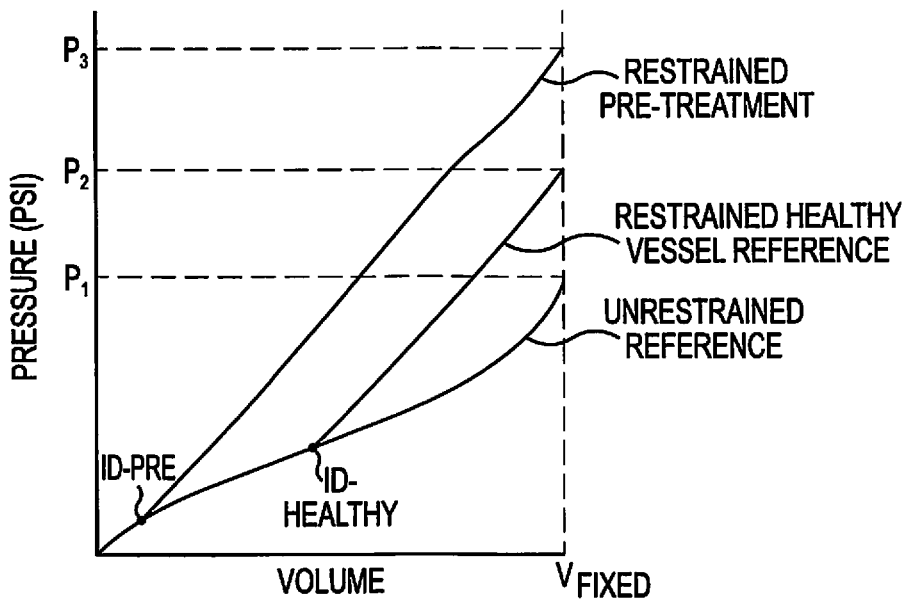
FIG. 3 illustrates the inflation compliance curve of an occluded vessel pre-treatment (restrained) biological conduit, e.g., a blood vessel with a lesion, compared with the unrestrained balloon reference curve from FIG. 1 and the restricted healthy biological conduit reference curve data from FIG. 2 with the same fixed inflation volume and rate.

Turning now to FIG. 3, a compliance inflation curve for a test occluded vessel is illustrated as restrained (pre-treatment) in combination with the restrained and unrestrained reference compliance curves discussed above. Pre-treatment indicates that, e.g., an occlusion is present and the removal process or treatment has not occurred. The balloon, matching that of one or both of the reference compliance curves (when both the unrestrained and restrained compliance curves are used) is employed together with the same fixed volume and inflation rate parameters used to generate the reference compliance curve(s) used. The unrestrained reference compliance curve and/or the restrained reference compliance curve may be used as illustrated. In some embodiments, as discussed above, the reference compliance curve(s) may be pre-stored in a database and/or memory of a computing device and accessible during the generation of the test data as in FIG. 3 for comparative analysis.

Analysis of the restrained pre-treatment vessel data proceeds in a similar fashion as discussed above when comparing the restrained and unrestrained reference compliance curves. The point of divergence of pressures at a given volume for the test restrained pre-treatment vessel occurs at a smaller volume than either the restrained healthy vessel reference or the unrestrained reference compliance curves. This point of divergence is marked as ID-pre and indicates the inner diameter for the restrained pre-treatment vessel, as derived from the restrained healthy vessel reference compliance curve and the unrestrained reference compliance curve. ID-pre is graphically smaller than ID-healthy. The data also indicates the relative size of the inner diameter of the restrained healthy reference compliance curve, marked as ID-healthy as indicated by its divergence of pressure at a given volume compared with the unrestrained reference compliance curve. Thus, a comparison may now be made between the healthy vessel inner diameter and the restrained pre-treatment vessel inner diameter which is clearly smaller than the healthy vessel's inner diameter as shown graphically in FIG. 3. The method for determining the inner diameter of the test vessel is done with comparison and reference to the OD table developed for any given volume and pressure for the unrestrained reference compliance curve as discussed above. Since the test and unrestrained reference balloons are of the same physical characteristics, and filled at the same inflation rate with the same fixed volume, the outer diameters of the two balloons will be the same so long as the point of divergence ID-pre has not been reached on the graph. This indicates that the vessel wall has not been encountered and so is applying no opposition force to the expanding test balloon. The inner diameter of the wall is, as discussed above, determined from the point of divergence ID-pre, where the wall is encountered by the expanding balloon. The easy and real-time graphical visualization of the relative pressures at given volumes and the relative inner diameters for the test vessel and the healthy reference vessel is important to enable surgical operator to see how different the test site is in terms of inner diameter than compared with a similar healthy vessel. In addition, the operator may readily see the area between the test and reference curves and the relative slopes for the curves and visually ascertain compliance or elasticity as well as the opposition force metrics. Alternatively, executable instructions for calculating each of the afore-mentioned metrics may be stored in the memory of a programmable computing device and executable by a processor that is in communication with the memory for display on a display device.

Thus, a comparison of the relative measured pressures at any point beyond the point of divergence ID-pre of the restrained pre-treatment vessel pressure from the restrained healthy vessel compliance curve of FIG. 3 may also be made. Clearly the restrained pre-treatment vessel pressure P3 is higher at any given volume beyond the divergence point than either the restrained healthy reference compliance curve's pressure P2 or the unrestrained compliance curve's pressure P1.

Further, the opposition force of the balloon used to generate the compliance curve for the restrained pre-treatment vessel may now be quantified as the area between the restrained pre-treatment compliance curve and the restrained reference compliance curve, beyond the point of divergence ID-Healthy of those compliance curves. Alternatively, the opposition force may be the delta P at any given volume between the restrained test compliance curve and the restrained healthy vessel reference curve, at any point beyond ID-Healthy.

Moreover, the elasticity, or compliance, of the vessel and/or the lesion therein that comprises the occlusion and used to generate the restrained pre-treatment compliance curve of FIG. 3 may be measured by comparing the slope of that curve with the slope of the restrained healthy reference compliance curve. As one would expect, the pre-treatment vessel and/or lesion has a higher slope of pressure change with increasing volume than does the restrained healthy reference vessel. This indicates a degree of loss of elasticity or compliance in the pre-treatment vessel as a result of the presence of the lesion as compared with the reference vessel and may be calculated at any point along the compliance curves for a given volume.

Figure 4:
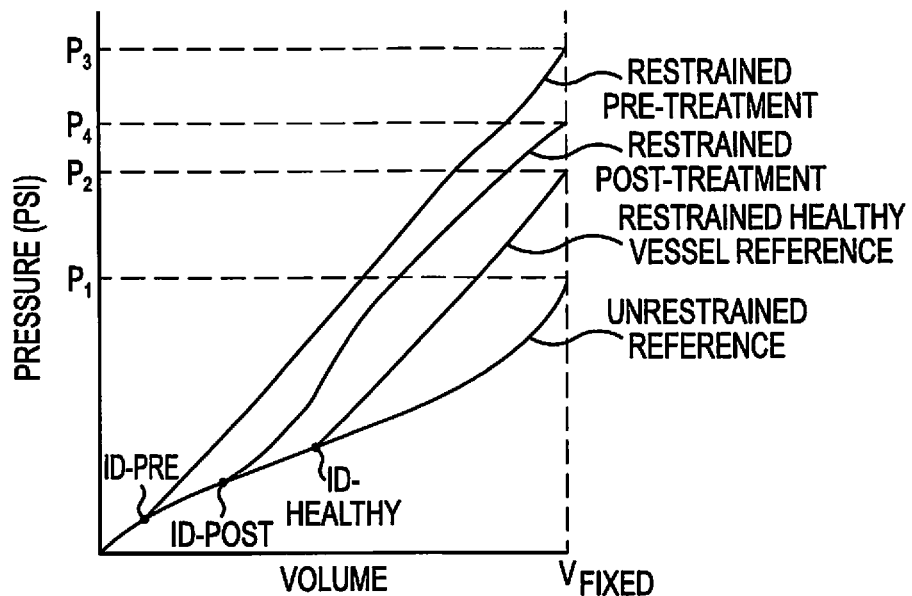
FIG. 4 illustrates the inflation compliance curve of an occluded biological conduit, e.g., a blood vessel with a lesion, post-treatment (restrained) compared with the unrestrained balloon reference curve from FIG. 1 and the restricted healthy vessel reference curve data from FIG. 2 with the same fixed inflation volume and rate.

FIG. 4 is similar to FIG. 3 except that now the test compliance curve is from a vessel that has some, or all, of the occlusive material removed, or undergone another procedure to increase inner diameter and/or compliance, i.e., is "post-treatment". Thus, the pressures of the retrained (post-treatment) compliance curve, restrained (pre-treatment), restrained healthy reference compliance curve and the unrestrained compliance curve may be compared as each compliance curve is generated using the same balloon or one with similar physical characteristics, the same fixed volume and the same inflation rate.

Consequently, the restrained post-treatment compliance curve's pressure P4 is illustrated as slightly higher than the compliance curve pressure P2 generated within the restrained reference healthy vessel and higher still than the pressure P1 generated by the unrestrained reference compliance curve, at any given volume beyond the relevant point of divergence at ID-post. The compliance curve for restrained pre-treatment from FIG. 3 is included for use in comparing its pressure P3 at a given volume after the point of divergence at ID-Healthy.

In addition to relative pressure data, the present invention also allows quantitation of the inner diameters (by the relevant points of divergence) of the restrained pre-treatment (ID-pre), the restrained post-treatment (ID-post) and the healthy reference vessel (ID-Healthy). As perhaps expected, ID-healthy is slightly larger than the restrained post-treatment inner diameter, while both ID-post and ID-healthy are significantly larger than ID-pre, indicating a successful procedure is at least underway.

The test data may be captured real-time during an occlusion removal procedure, or other procedure designed to increase a vessel's diameter and/or its compliance in order to enable the graphical comparison and display as discussed above. In the case of the data of FIG. 4, the operator may determine that further atherectomy, angioplasty, or other procedure may be needed since the real-time data indicates that ID-healthy is still larger than ID-post, the opposition force for the restrained post-treatment compliance curve is larger than healthy vessel reference compliance curve. Further, the compliance or elasticity of the restrained post-treatment compliance curve, as determined by the relative steepness of its slope, may be less than the restrained healthy vessel compliance curve, thereby providing data on the compliance of the vessel and/or lesion post-treatment.

As discussed above, graphical display of the compliance curves as well as, in alternative embodiments, the calculation and display of the inner diameter, opposition force and compliance/elasticity metrics is a great aid to the operator in determining what, if any, additional work is required to optimize the occlusion removal or other similar procedure.

Figure 5:
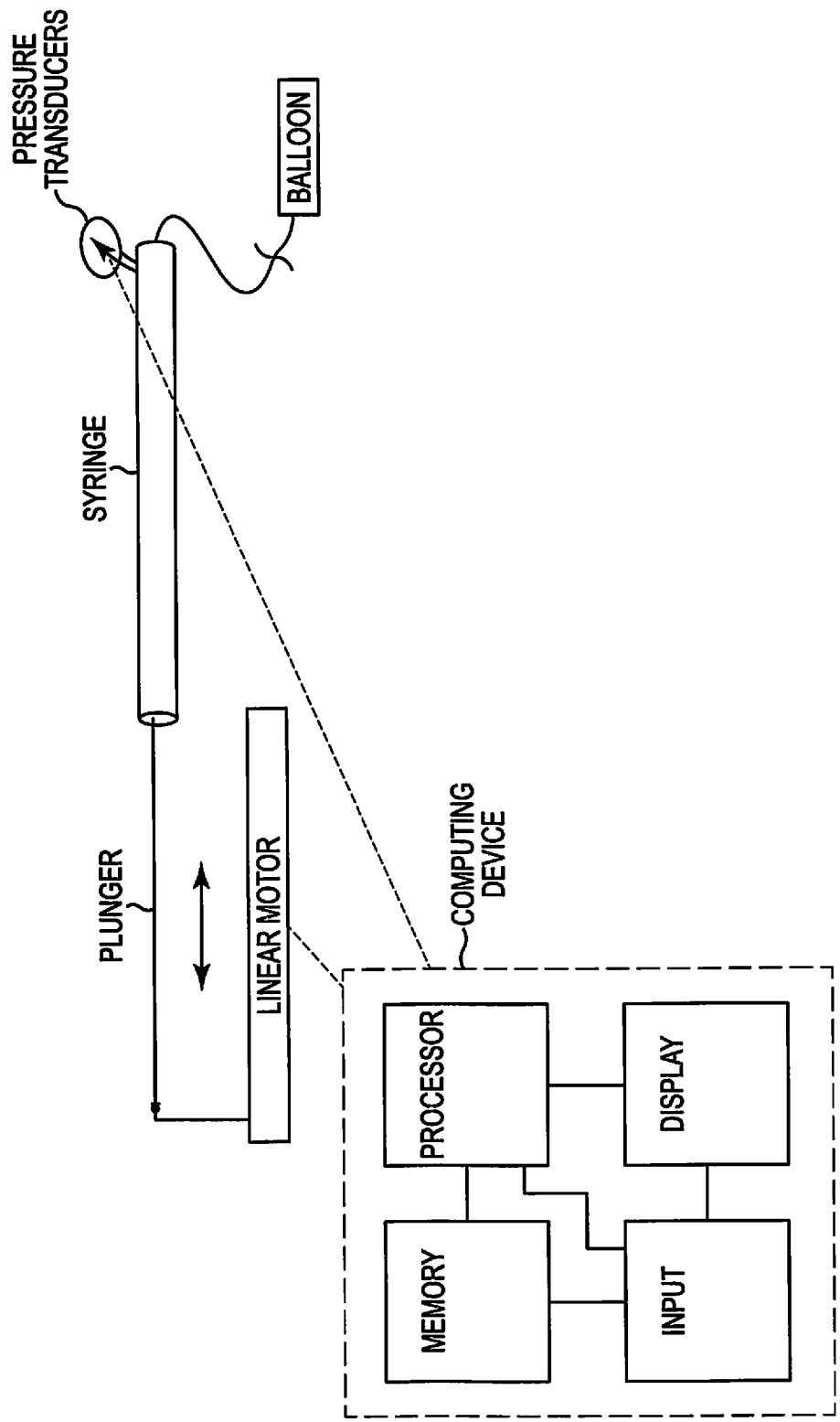
FIG. 5 illustrates one embodiment of a device and system of the present invention.

The functionality of the above method may be achieved using a variety of devices. The required elements consist of a balloon of known elasticity, or compliance, a device, e.g., a syringe, that is capable of injecting a known and fixed volume of fluid to inflate the balloon at a known and fixed rate, a pressure transducer in operative communication and connection with the inflating balloon to measure the pressure experienced by the balloon as it inflates. One such exemplary system is illustrated in FIG. 5. There is illustrated an exemplary linear motor that is capable of translating the plunger of syringe at a fixed rate. Alternative means of providing a constant, known inflation rate are also known and within the scope of the present invention. The syringe is filled with a known and fixed volume of fluid for inflating a balloon. A pressure transducer is in operative communication and connection with the balloon to measure and display and/or record the pressure data as well as the corresponding volume data.

In certain devices, a wireless control device as is known in the art may be used to control the linear motor, or other means of providing constant and known inflation rates.

The operator may also input data into the computing device, e.g., a preselected desired opposition force may be selected and input into the computing device. The result is an automatic inflation of the balloon to the selected opposition.

The device may further have the ability to learn, and store, compliance curve profiles for various balloons and device for ease of access during subsequent procedures.

Alternative devices and/or systems may be employed. For example, the pressure and volume data may be output to a programmable computing device and stored in a memory within the computing device. The stored data may be then subjected to programmable instructions that are stored within the device's memory and that, when executed by a processor in operative communication with the memory, an input such as a keyboard or the like and a graphic display, transform the data into the graphical form as illustrated in the Figures herein. The reference compliance curve(s) may also be stored in the device's memory and graphically displayed along with the test data for visual comparison with the key metrics marked and highlighted for ease of visualization. For example, the inner diameter size quantitation for the test data's compliance curve may be illustrated, pre-treatment and/or post-treatment, and compared with that of a healthy reference compliance curve, to assist in determining if the procedure is complete. Additionally, the opposition force, as describe herein, may be measured, quantified and displayed in real time to allow the operator to determine procedural progress. Moreover, the compliance, or elasticity of the vessel may be measured, quantified and graphically displayed as a slope comparison with the reference compliance curve as described herein.

Fractional Flow Reserve (FFR) may also be used in various embodiments of the present invention to obtain functional measurements of a biological conduit and the area of interest therein, e.g., a blood vessel with an exemplary lesion therein.

Measurement of compliance and elastance of the exemplary blood vessel with lesion are disclosed herein. The primary aspect of this embodiment of the present invention is to provide measurement of compliance and/or elastance of a biological conduit, e.g., blood vessel, and an area of interest therein, e.g., a lesion, for use in integrated combination with a procedure within the conduit's area of interest.

For example, a vascular procedure comprising, without limitation, atherectomy procedures—including rotational atherectomy procedures, angioplasty, stent placement and biovascular scaffolding. All other procedures involving evaluation, reduction, remodeling and/or removal of a lesion or occlusion are also within the scope of procedure or vascular procedure.

Thus, FFR is a technique used to measure pressure differences across, e.g., a stenosis or lesion within an exemplary artery to determine the likelihood the stenosis is impeding oxygen delivery to organs and tissues located distal to the lesion. FFR is defined as the pressure behind (distal to) a lesion relative to the pressure in front of (proximal to) the lesion. The result is an absolute number; an FFR of 0.80 means a given lesion causes a 20% drop in blood pressure. Pressure sensors and FFR are well-known to the skilled artisan. For example, pressure sensors that may be used in FFR techniques are described in more detail in U.S. Pat. Nos. 5,450,853; 5,715,827; 5,113,868; 5,207,102.

Flow velocity within a conduit, e.g., blood vessel, may also be measured by known devices and techniques. See, e.g., U.S. Pat. Nos. 4,733,669; 5,125,137; 5,163,445 for exemplary flow sensors that may be employed.

Finally, resistance to flow within a conduit, e.g., blood vessel, may be measured by known devices and techniques used for FFR and flow velocity as a localized resistance value, e.g., in a region of interest comprising a lesion within a blood vessel, may be calculated as the change in pressure (proximal to the lesion vs. distal to the lesion) divided by the flow. Thus, as the exemplary vascular procedure proceeds, the resistance waveform will begin to change and may be used as an indication of changing compliance of the lesion and/or vessel.

Pressure, flow velocity and resistance to flow measured within a conduit, e.g., blood vessel, are parameters that are dependent in part upon compliance and elastance, each parameter manifesting in a diagnostic waveform. It is significant to the present invention that at least one of the pressure, flow velocity and resistance-to-flow waveforms in a non-compliant vessel differs from that of a compliant (healthy) vessel due to dampening of the velocity waveform, the pressure waveform and the resistance waveform. Consequently, the changes in flow velocity, pressure and resistance waveforms during a procedure, e.g., a vascular procedure, to change the compliance and/or elastance of the vessel and/or exemplary lesion therein, directly reflect the compliance and/or elastance changes resulting from the procedure and may be monitored therefore.

Functional implications: Arterial compliance (C) and distensibility (C/A) are given by the slope of the non-linear relation between the transmural pressure (p) and the luminal cross-sectional area (A), an expression of the elastodynamic coupling between the blood flow dynamics and vessel wall mechanics. The speed of the pressure wave, which is inversely proportional to the square root of the wall distensibility, can be also computed using the Moens-Korteweg equation. Arterial calcification adversely affects blood flow dynamics and vessel wall mechanics. Arterial medial calcifications have several major consequences according to the diseased arterial compartment. In the macrocirculation stiffening of the arterial wall is associated with increase in pulse wave velocity, increase in pulse pressure and pulsewave deformation (premature wave reflection, diastolic decay steepening).

Figure 6:
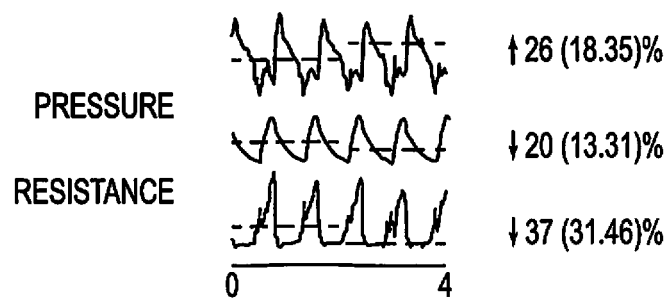
FIG. 6 illustrates waveforms for flow velocity, pressure, and resistance.

FIG. 6 provides an example of waveforms changing during modification of vessel and/or lesion compliance achieved during a procedure or a vascular procedure. The waveforms comprise measured parameters of flow velocity (measured with flow sensors), pressure (measured with pressure sensors and FFR techniques) and flow resistance to assist in determining whether a change in compliance has been effected as well as determining or assessing whether the compliance change indicates that sufficient compliance has been restored by the procedure or vascular procedure.

Figure 7:
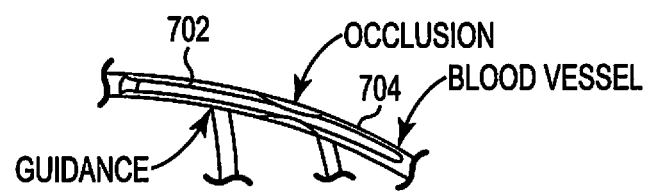
FIG. 7 illustrates a partial cutaway view of a prior art device in operation.

FIG. 7 illustrates an exemplary FFR pressure monitoring guide wire with at least one pressure sensor disposed along the wire and proximate the distal radiopaque tip and disposed within an exemplary blood vessel with occlusion. The pressure sensor is integrated into the device with an exemplary torque device for conducting an exemplary rotational atherectomy procedure. In the illustrated embodiment, distal pressure sensor 702 is located distal to the occlusion and proximal pressure sensor 704 is located proximal to the occlusion. Note that the FFR measurements and, therefore, the compliance and/or elastance measurements, may occur before, during and/or after the exemplary vascular procedure. Similarly, a monitoring wire may comprise flow sensor(s) (not shown but as well known in the art) along the wire, either replacing the pressure sensors or in combination therewith, wherein the flow velocity is measured proximal and distal to an exemplary lesion before, during and/or after a vascular procedure to determine change in compliance and/or elastance of the lesion and/or vessel. The FFR may be calculated, as is well known, as the ratio of the distal and proximal pressure sensor measurements.

A set of monitored parameters, e.g., flow velocity, pressure, and/or flow resistance may be taken within the same or similar conduit or vessel in order to establish at least one set of reference compliance data for the subject patient. Alternatively, a library of pre-determined normal data may be established for a variety of conduit, e.g., vessel, sizes and types which may be stored as at least one set of reference compliance data to use for the subject patient. Both, or either, of these types of reference compliance data sets may be stored and accessed during the exemplary vascular procedure for reference purposes and comparison with test compliance data obtained before, during and/or after the vascular procedure.

These reference compliance data, whether taken from a pre-determined library or from the same or similar vessel directly, may be used as reference points to assist the procedure, e.g., vascular procedure, operator in determining the type or composition of a lesion within the exemplary vessel, the best type of vascular procedure to use given the type and/or composition of the lesion as well as the best tool to execute the vascular procedure. For example, a rotational atherectomy device may be indicated based on the type or composition of lesion. Further, the lesion type of composition may indicate the sizing of torque device, speed of rotation and type of abrasive element, e.g., concentric, non-concentric, to use during the atherectomy procedure. In addition, these data may provide indication during the procedure, e.g., the vascular procedure, when the lesion and/or vessel compliance begins to change in response to the exemplary vascular procedure. These compliance changes may be evaluated after an initial running of the exemplary procedure, before and after the exemplary procedure, and during the exemplary procedure. Ultimately, these data may provide indication, in some cases real-time indication, that the vessel and/or lesion compliance and/or elastance is within normal limits as determined by comparison of the test compliance or elastance data sets with the at least one reference compliance data sets.

Figure 8:
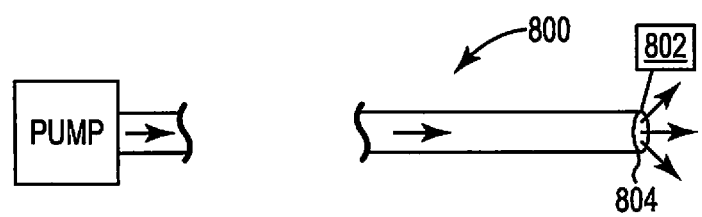
FIG. 8 illustrates a side cutaway view of one embodiment of the present invention.

FIG. 8 illustrates an embodiment wherein the flow of a fluid, e.g., saline, through the vascular procedure system 800, e.g., a rotational atherectomy system, may be monitored by pressure and flow monitor 802 disposed at the tip 804 for changes in pressure as well as flow rate at the tip 804 of the system 800. In this embodiment, changes in pressure and flow may be monitored and compared with at least one reference data set.

Other methods, devices and systems comprising a created magnetic field, and changes thereof, allow evaluation and assessment of the lesion type and composition, positional estimates of a spinning rotational device within a conduit, e.g., blood vessel as well as allow measurement of compliance and, therefore, elastance, in real time. A preferred embodiment comprises creation of an AC magnetic field emitted by a permanent magnet embedded in an orbital atherectomy device abrasive element, e.g., crown or burr. We discuss this concept in relation to rotational atherectomy, however, the skilled artisan will recognize that the disclosed concept will work well with any rotational device working within a biological conduit, e.g., blood vessel. Thus, use of the disclosed devices, systems and methods with any rotational device working within a biological conduit is within the scope of the present invention.

During the orbital atherectomy procedure a doctor does not have good information on the increasing size of the vessel, e.g., artery opening as the procedure progresses. It would be desirable for the doctor to have real-time feedback as the artery opening is increasing in size during the procedure.

Solution to Problem: Permanent Magnet(s) Embedded in Spinning Crown.

Figure 9:
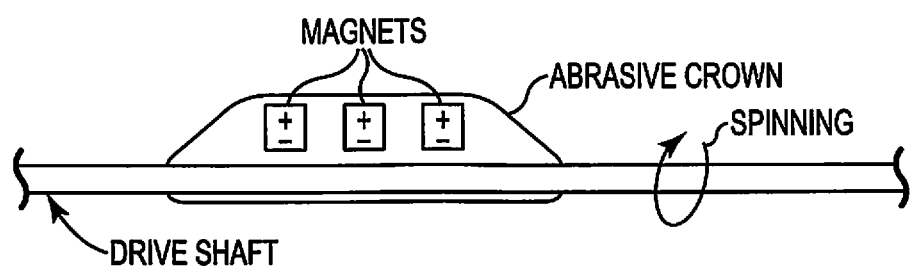
FIG. 9 illustrates a side cutaway view of one embodiment of the present invention.

One or more magnets are in, on or near the abrasive head, or crown, of the rotational orbital atherectomy device as shown in FIG. 9. Alternatively, the crown is composed of a magnetic material. An AC magnetic field will be emitted, as will be discussed further infra, as the crown spins or rotates. This AC magnetic field is the carrier signal. An AC magnetic field sensor which is substantially in the plane perpendicular to the axis, e.g., the longitudinal axis of the rotating abrasive head or crown, of the spinning magnet and placed substantially at a right angle to the axis of crown spin will be most sensitive to the emitted carrier signal.

Figure 10:
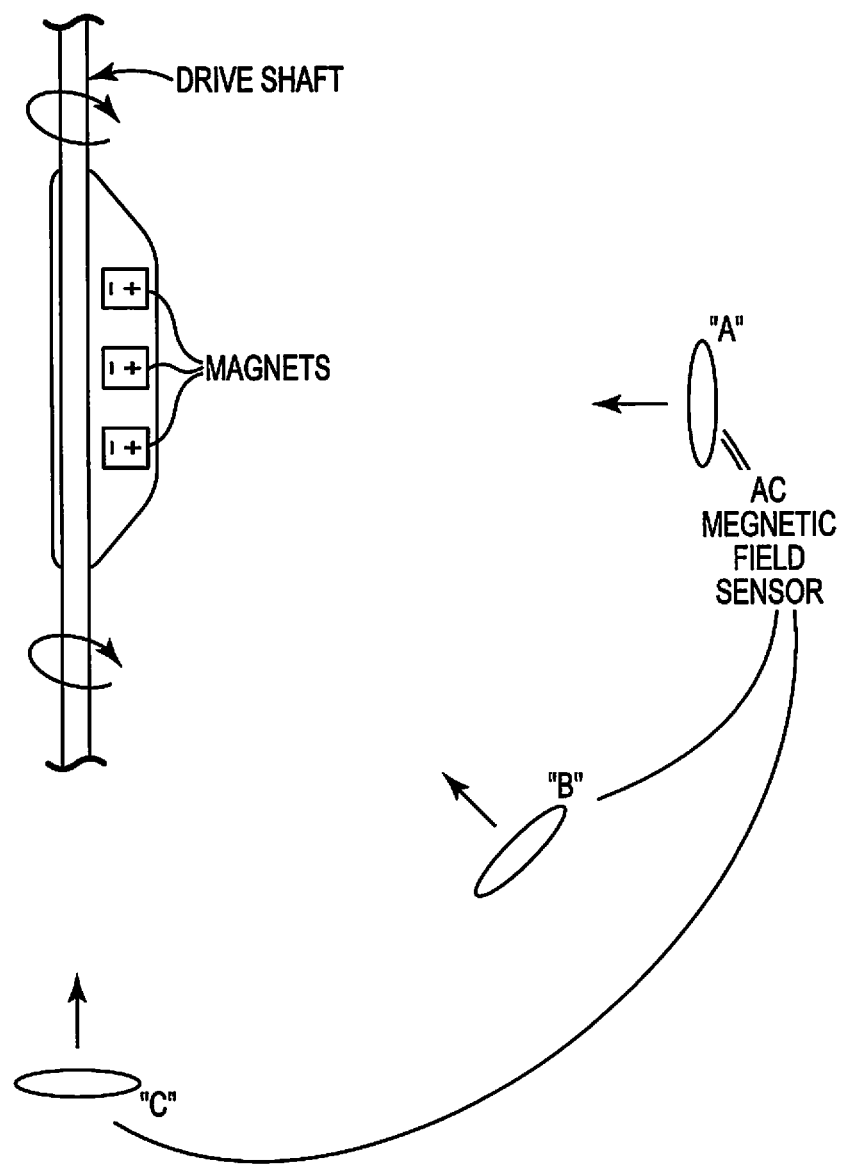
FIG. 10 illustrates a side cutaway view of one embodiment of the present invention.

As shown in FIG. 10, three sensors are placed at the same distance from the magnets inside the spinning crown. Sensor "A" is in the plane of the spinning magnet and will receive the strongest signal of the three sensors A, B & C. Sensor "C" is placed essentially along the axis of rotation and will detect little or none of the emitted AC magnetic field.

In practice, the AC magnetic field sensor(s) would be outside the body but positioned as close as reasonably possible to the spinning crown while still being as close to the plane of the spinning crown as possible.

Figure 11A:
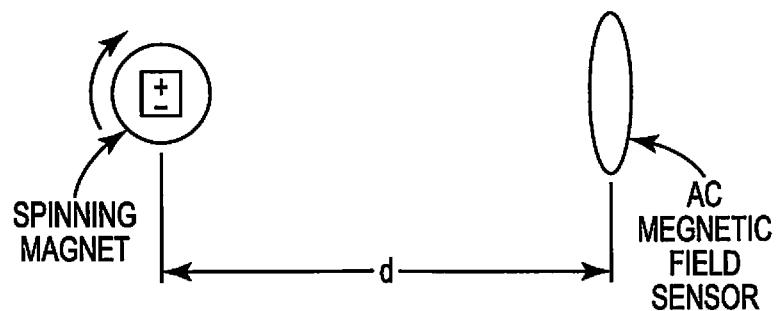
FIG. 11A illustrates a cutaway view of one embodiment of the present invention.
Figure 11B:
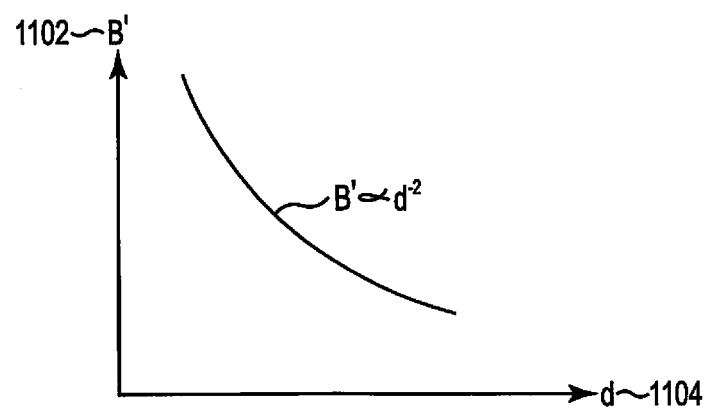
FIG. 11B illustrates a graphical relationship between two variables relevant to the present invention.

As the spinning crown moves relative to an AC magnetic sensor the carrier signal strength will change. The carrier signal strength will increase as the magnet-sensor distance, d, decreases. This relationship for a far-field situation will be approximately $B' \propto d^{-2}$, where B' is the signal strength 1102 detected by the AC Magnetic Field sensor and d is the distance 1104 between the spinning crown and the AC Magnetic Field Sensor. Note that the exponent for D may also be approximately −3. The illustrative equations used herein express distance d with the exponent −2, but as the skilled artisan will readily understand, the relationships may also comprise distance d with exponent −3. These relationships are illustrated in FIGS. 11A and 11B.

The carrier signal strength, B', will change depending on the relative orientation of the spinning crown and the AC magnetic field sensor. The influence of such systemic noise factors can be largely removed by taking the first order term of the Taylor series approximation of $B' \propto d^{-2}$, which is $\Delta B' \propto -2 \cdot d^{-3} \cdot \Delta d$ and dividing the two proportionalities which yields the equation $$\frac{\Delta B'}{B'} = -2 \cdot \frac{\Delta d}{d}.$$

Figure 12A:
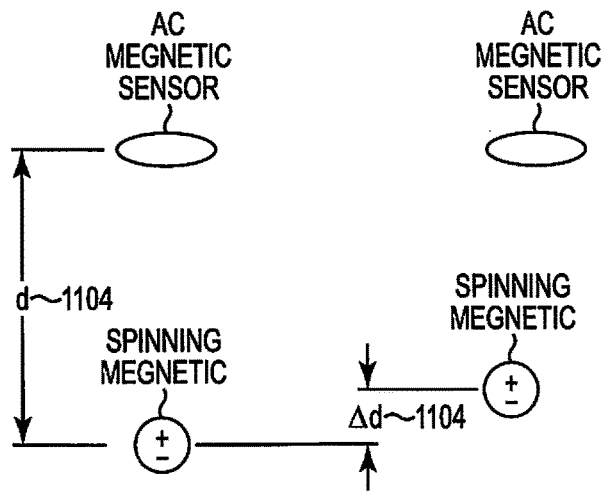
FIG. 12A illustrates a cutaway view of one embodiment of the present invention.
Figure 12B:
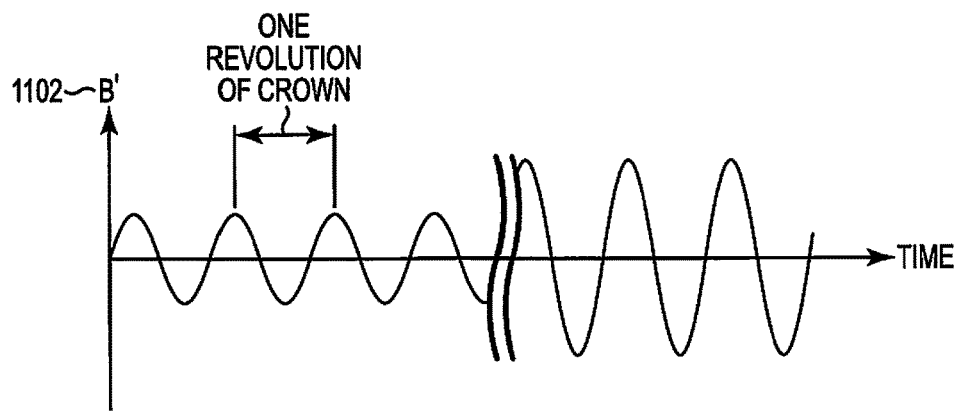
FIG. 12B illustrates a signal generated and detected by one embodiment of the present invention over time.
Figure 12C:
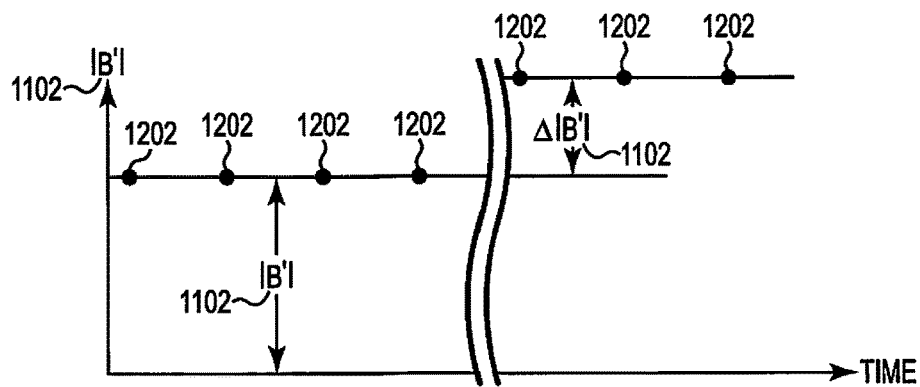
FIG. 12C illustrates a graphical peak to peak magnitude of a carrier signal of the present invention.

The interpretation of this equation is shown in FIGS. 12A-12C. On the left side of FIG. 12A is shown a spinning magnet which is a distance, d, from an AC magnetic sensor. On the right side of FIG. 12A, the distance between the spinning magnet and the AC magnetic sensor has been decreased by $\Delta d$. FIG. 12B shows the raw signal as detected by the AC magnetic sensor where each cycle of the signal corresponds to one revolution of the spinning magnet. The magnitude of the carrier signal on the left side of FIG. 12B corresponds to the distance, d, and the slightly larger magnitude carrier signal on the right side of FIG. 12B corresponds to when the distance between the spinning magnet and AC magnetic sensor has been decreased by $\Delta d$.

Detecting Small Movements of the Spinning Magnet

FIG. 12C shows the peak-to-peak magnitudes 1202 of the carrier signal, |B'|, on the left for the case where the spinning magnet and AC magnetic sensor are separated by distance, d, and the slightly larger magnitude of the carrier signal on the right for the case where the distance has been decreased by $\Delta d$. If any three of these quantities are known the fourth can be calculated from $$\frac{\Delta |B'|}{|B'|} = -2 \cdot \frac{\Delta d}{d}.$$

This relationship is used to estimate small movements of the spinning crown, $\Delta d$, over a short period of time.

$$\Delta d = -\frac{d}{2} \cdot \frac{\Delta |B'|}{|B'|}$$

Estimating One Dimension of a Space which is Constraining the Spinning Magnet.

A conceptual extension of this relationship applies to a spinning magnet which is freely orbiting or moving within a constrained space over a short interval of time.

Figure 13A:
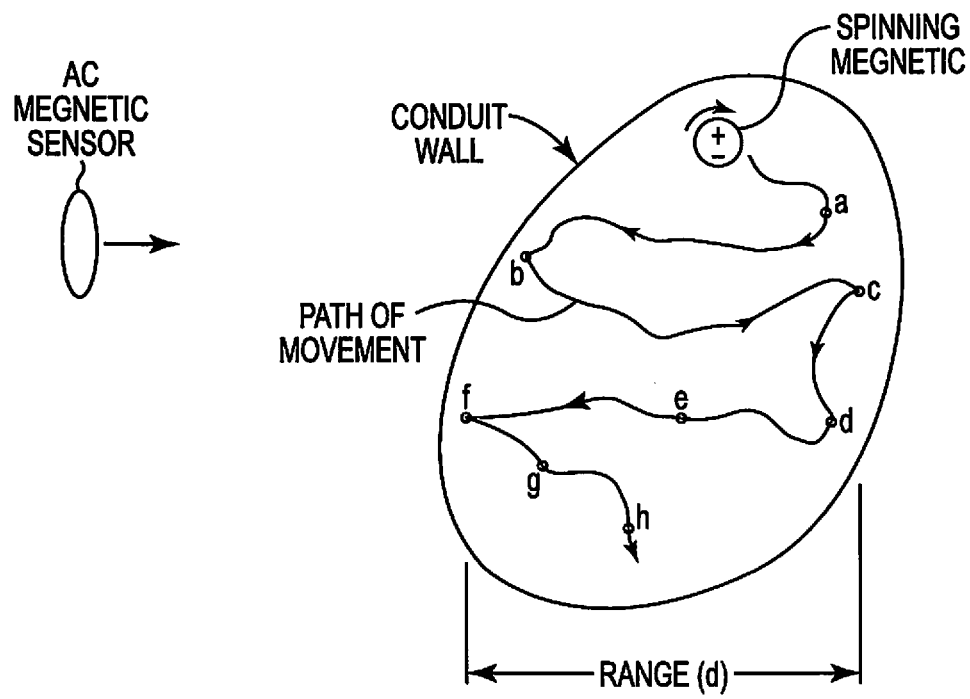
FIG. 13A illustrates an exemplary orbital path taken by one embodiment of the present invention.
Figure 13B:
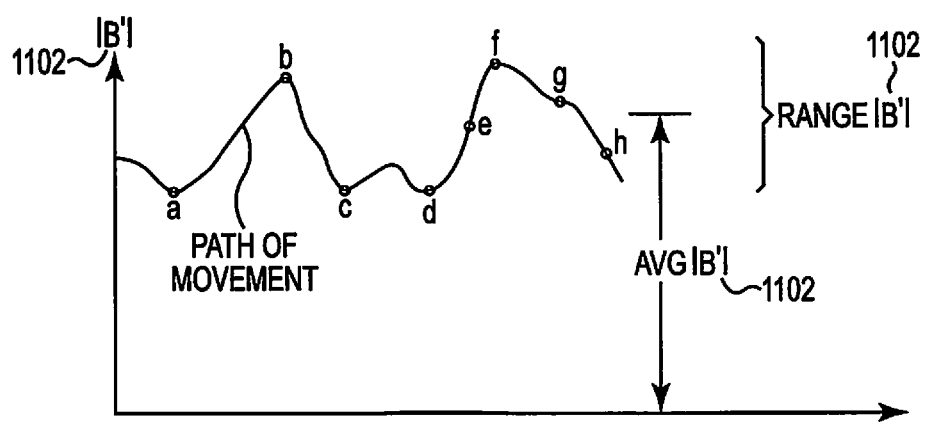
FIG. 13B illustrates graphically the detected peak-to-peak signal generated and detected by the embodiment of FIG. 13A.

In this case the detected carrier signal magnitude, |B'|, will vary as the spinning magnet moves along a path (points "a" thru "h") relative to the AC magnetic sensor as shown in FIG. 13A. The detected peak to peak carrier signal strength is shown in the graph of FIG. 13B with points "a" thru "h" marked as the spinning magnet travels along the path. The variation in |B'| can be estimated over the time interval of interest in some way such as the range of carrier signal magnitudes, Range|B'|. An estimate of the signal magnitude, |B'|, can simply be the average, AVG|B'|, over the time interval of interest.

$$\text{Range}(d) = -\frac{d}{2} \cdot \frac{\text{Range}|B'|}{\text{AVG}|B'|}$$

In this manner the dimension of the constraining space can be continually estimated as the spinning magnet moves around within the constraining space.

There are several options for calculating variation estimates of |B'| such as interquartile range, (90%-10%) and standard deviation. In practice it may be useful to use non-parametric metrics for both the variation and point estimates which are less susceptible to outlier data points and other noise.

Estimating the Dimensions of a Space which Constrains the Spinning Magnet.

Figure 14:
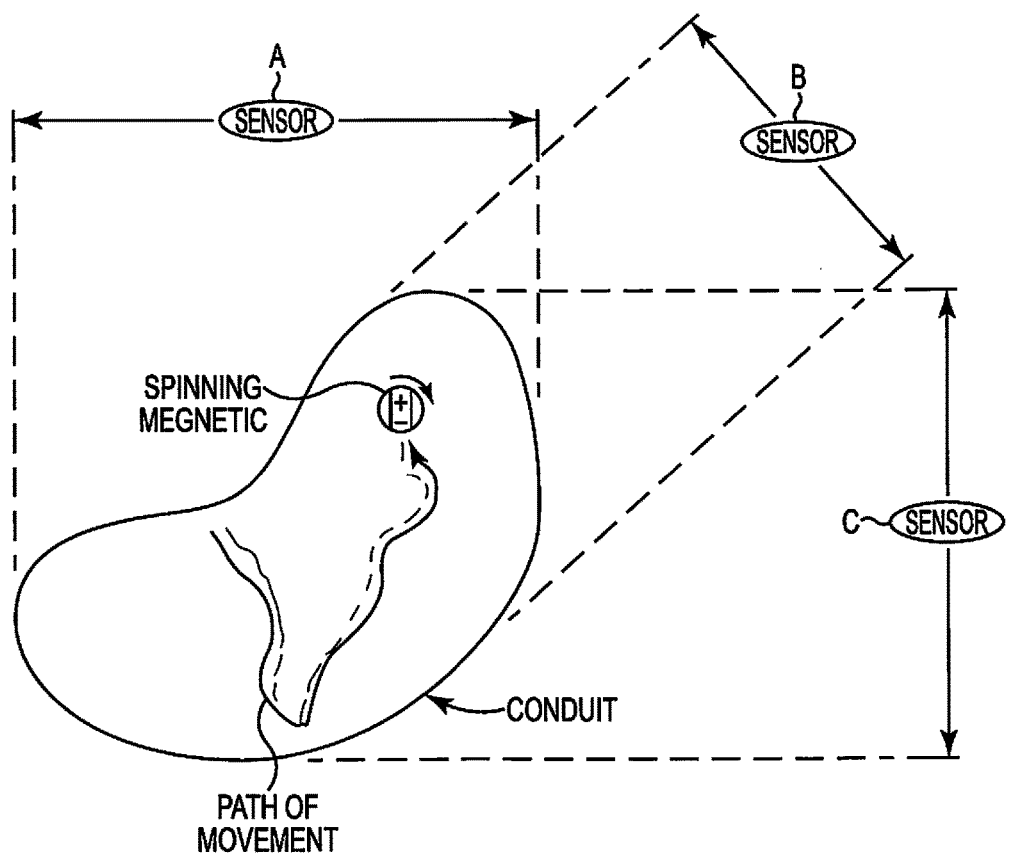
FIG. 14 illustrates an embodiment of the present invention.

A sensor can be used to estimate the dimension of a constraining space, such as an artery opening, only in the direction from the sensor to the spinning magnet. 2 or more sensors can be positioned around the constraining space to obtain multiple estimates of the opening size from different perspectives. FIG. 14 illustrates an example where three AC magnetic sensors: "A", "B" & "C" are used to obtain multiple independent dimensional estimates and shows a kidney-shaped constraining space or conduit. In the case where the information from multiple sensors are considered independently it would be very difficult to determine the shape of the constraining space was kidney-shaped as opposed to an ellipsoid type of shape. Alternatively, there are demodulation methods which are common in communications systems and signal processing which are well-suited to this situation.

Estimating the Shape of a Constraining Space.

When using two or more sensors it is possible to use the sensor data to estimate the shape of the space or conduit constraining the movement of the spinning magnet within the space or conduit.

Figure 15A:
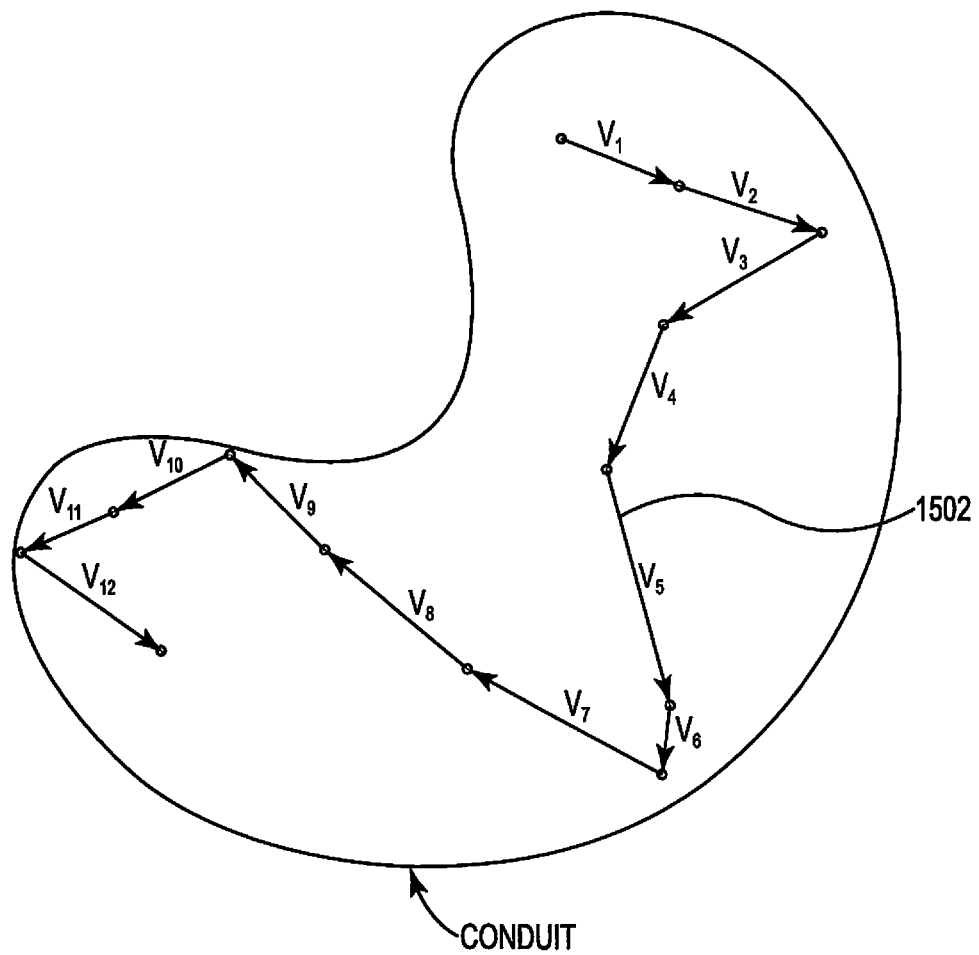
FIG. 15A illustrates movement vectors for an embodiment of the present invention.
Figure 15B:
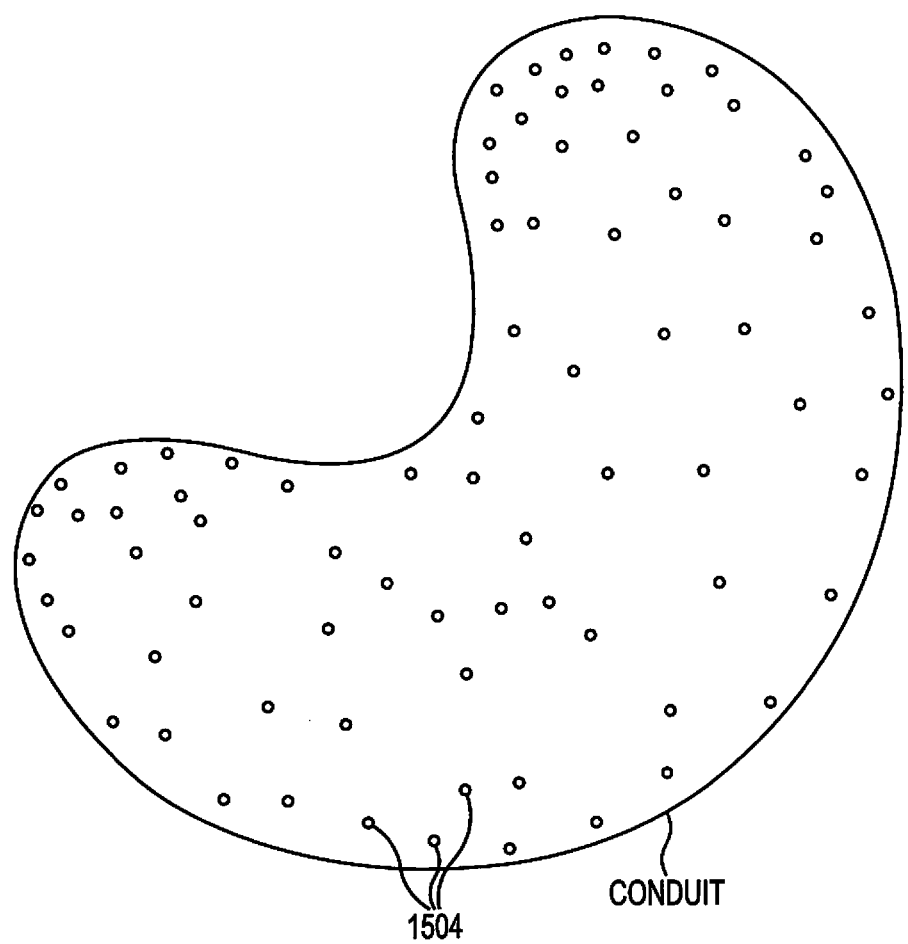
FIG. 15B illustrates a density of detected positions for an embodiment of the present invention.

Two or more sensors, as illustrated supra, may be used to derive a vector of movement for each revolution of the spinning magnet. The simplest case is two sensors mounted at right angles to each other relative to the sensor but this concept can be generalized if more sensors are available or if the two sensors are not at right angles to each other. The movement vectors 1502 from successive revolutions of the spinning magnet can be pieced together to create a path of movement within a constrained space as illustrated in FIG. 15A. If a path of movement is tracked for a sufficiently long period of time the density of detected positions 1504 will define the shape of the constraining space as illustrated in FIG. 15B.

In the case where magnets are incorporated into the crown, it may be desirable to use a material for the crown which is devoid of ferromagnetic material unless the crown's ferromagnetic material is magnetized such that the crown's magnetic field aligns with the magnetic field of the magnets. Alternatively, the crown could be constructed of a material, such as a ferromagnetic, which can be magnetized. Alternatively, the crown could be simply non-metallic to mitigate interference of the emitted signal.

Indication of Artery Wall Calcification

During the orbital atherectomy procedure a doctor does not have good information on the composition of the artery wall which is being treated as the procedure progresses. It would be desirable for the doctor to have real-time feedback as the composition or calcification of the artery wall during the procedure.

The emitted carrier wave will be very sensitive to abrupt speed or position changes of the crown. This sensor behavior could manifest in at least four different ways which could be used to identify the artery wall material which the crown contacts.

Figure 16:
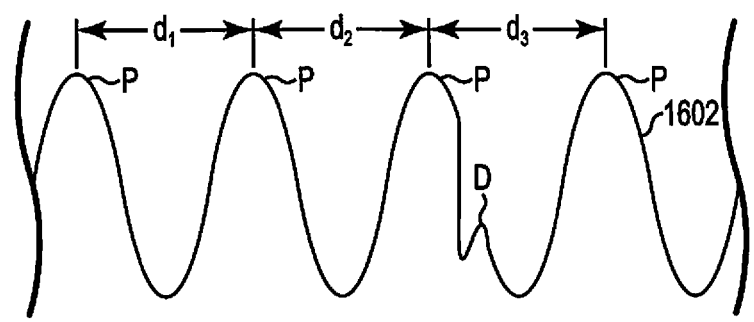
FIG. 16 illustrates one embodiment of a magnetic carrier wave of the present invention.

First, the crown spin-rate may briefly slow down when it contacts one type of wall material as opposed to others. This brief slowing down and speeding back up would appear as a disturbance D in the carrier wave 1602 as shown in FIG. 16. In this case, distance from peak p to peak p of vectors 1502 may increase. Thus distance $d_1=d_2<$distance $d_3$. For example, there may be a great deal of friction as the spinning crown contacts calcium which causes it to briefly slow and exhibit this signature behavior.

Figure 17A:
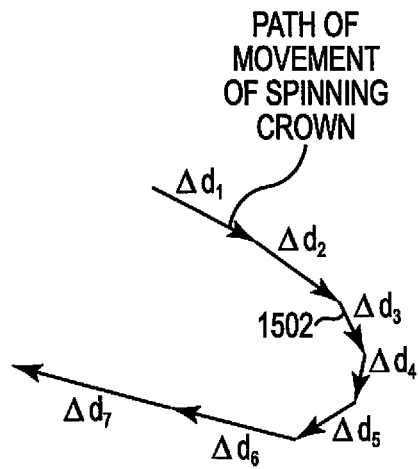
FIG. 17A illustrates an orbital path for one embodiment of the present invention.
Figure 17B:
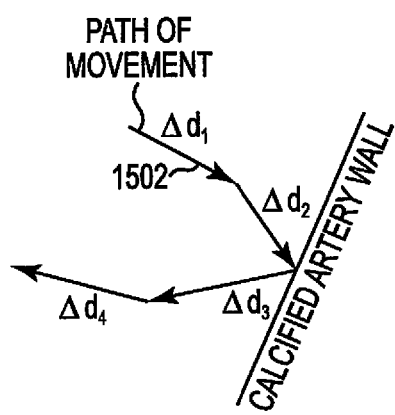
FIG. 17B illustrates an orbital path for one embodiment of the present invention.

Second, the spinning crown may bounce off a calcified wall differently than it would bounce of a healthy artery wall or a partially calcified wall given that the composition of the wall is closely related to the compliance of the wall. FIG. 17A is an illustration of how a spinning crown might slowly rebound from a healthy and highly compliant artery wall. In contrast, FIG. 17B is an illustration of the detected Δd's of movement vectors 1502 that would be detected for a spinning crown which sharply bounces off non-compliant calcified wall.

Figure 18A:
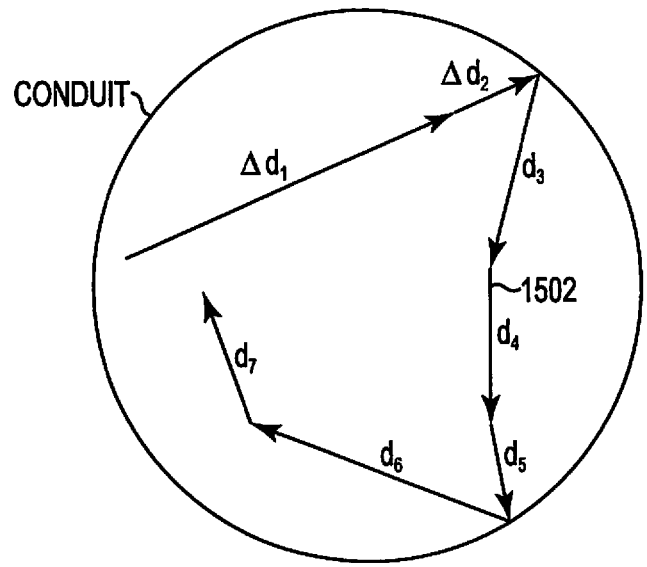
FIG. 18A illustrates an orbital path for one embodiment of the present invention.
Figure 18B:
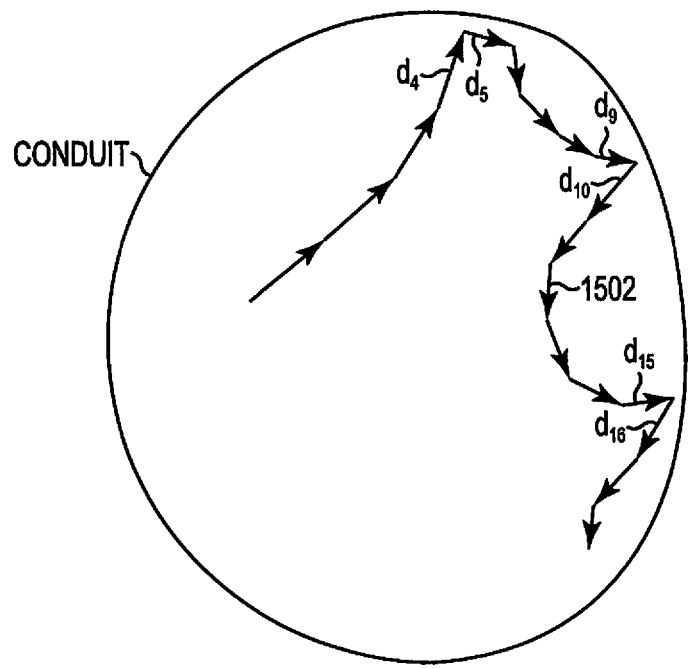
FIG. 18B illustrates an orbital path for one embodiment of the present invention.

Third, the speed and pattern of general movement of the spinning crown within a confining space may be quite different if the artery walls are healthy or calcified. FIG. 18A illustrates the path of a crown which is moving very rapidly around within the confined space as it bounces off rigid, calcified walls whereas FIG. 18B illustrates a crown which is very slowly moving within a similar confined space (not shown) as it slowly rebounds from the soft and compliant walls of a healthy artery, as indicated by the Δd's of movement vectors 1502.

Figure 18C:
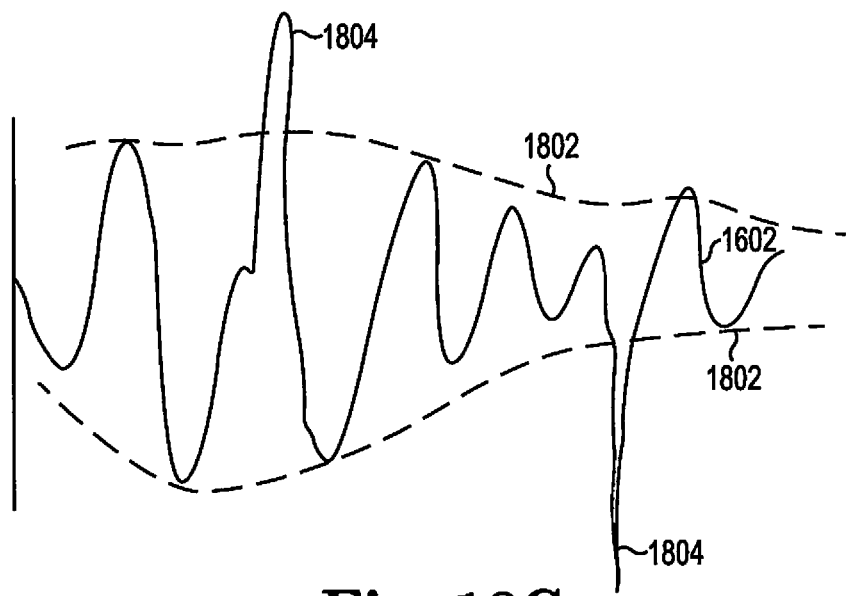
FIG. 18C illustrates graphically one embodiment of a magnetic carrier wave of the present invention.
Figure 18D:
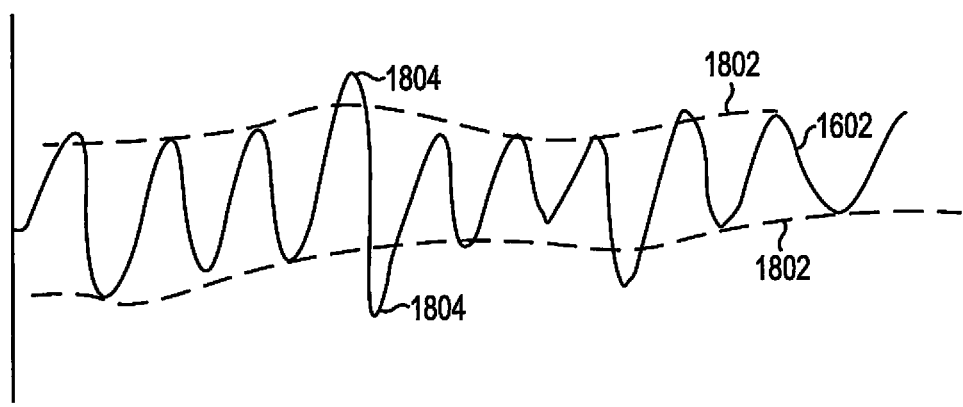
FIG. 18D illustrates graphically one embodiment of a magnetic carrier wave of the present invention.

Fourth, in the case of the second and third examples given above, the indicator of calcification would be primarily based on the path of motion. However, in both of these cases the recoil from a soft, compliant wall and a hard calcified wall may also manifest more directly in the carrier wave signal 1602 as shown in FIGS. 18C and 18D. FIG. 18C illustrates how the carrier wave 1602 may spike 1804 well outside the general average peak-to-peak envelope 1802 when the spinning crown makes contact with a hard wall. FIG. 18D illustrates how the carrier wave peak to peak amplitude on each cycle will remain more or less within the peak-to-peak envelope when the spinning crown makes contact with a soft, compliant healthy artery wall, though spikes 1804 may occur.

The signal-to-noise of the detected AC magnetic carrier signal may be poor depending on factors such as the distance from the spinning magnet to the AC magnetic field sensors.

If the signal-to-noise is poor then it may be necessary to use rotational position sensor data from the motor to phase lock onto the AC magnetic carrier signal.

It is possible for the crown to be pushed into an occlusion such that it stalls the device. It would be desirable to have an indication of an impending stall.

Use of Motor Rotational Position as an Indication of Loading on Shaft and Impending Stall.

One possible means of detecting an impending stall would be to compare the rotational position of the crown with the rotational position of the motor. The difference in the rotation positions would be a function of the torque on the shaft due to loading on the crown which could be used to indicate an impending stall.

Figure 19:
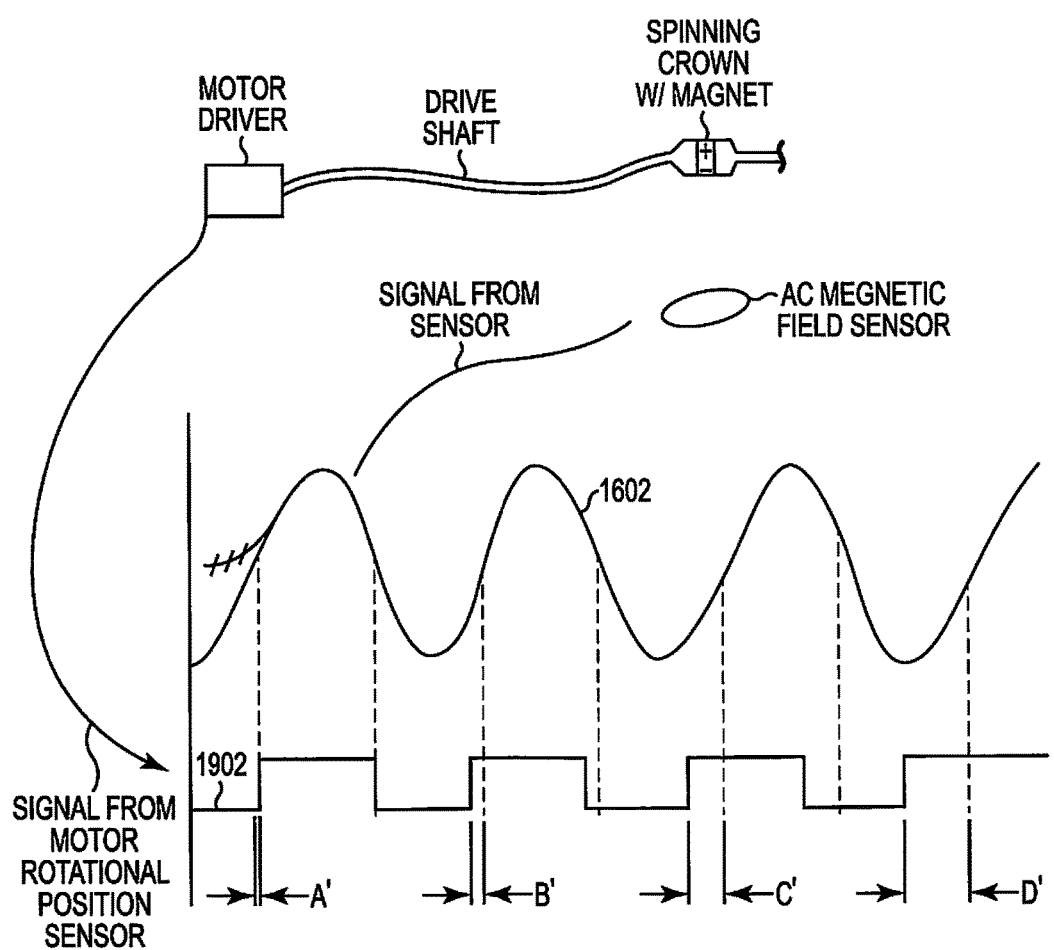
FIG. 19 illustrates one embodiment of the present invention with graphical representation of a magnetic carrier wave of the present invention.

In contrast to the section above it is possible the signal-to-noise of the detected AC magnetic carrier signal may be excellent. In this case the near-instantaneous crown rotational position can be determined from the carrier wave. The near-instantaneous motor rotational position can be determined from output signal 1902 available from the motor driver. Comparing the Crown and Motor rotational position is an indicator of the load on the drive shaft. If the phase lag between the motor and the Crown increases it may indicate the Crown is being pushed into material which is causing increased drag and may be approaching a stall. FIG. 19 illustrates this concept as the phase lag is shown to increase on each rotation of the crown as indicated by "A'"<"B'"<"C'"<"D'".

The quantitative estimate of the dimensions of the constraining space is dependent on the accuracy of the distance between the AC magnetic sensor and the spinning magnet. Given that there will likely be several such sensors on or near the skin surface and the wide range of anatomical variation the distance to the magnet for each sensor will change with the patient.

Self-Calibrating AC Magnetic Sensor Array

Figure 20:
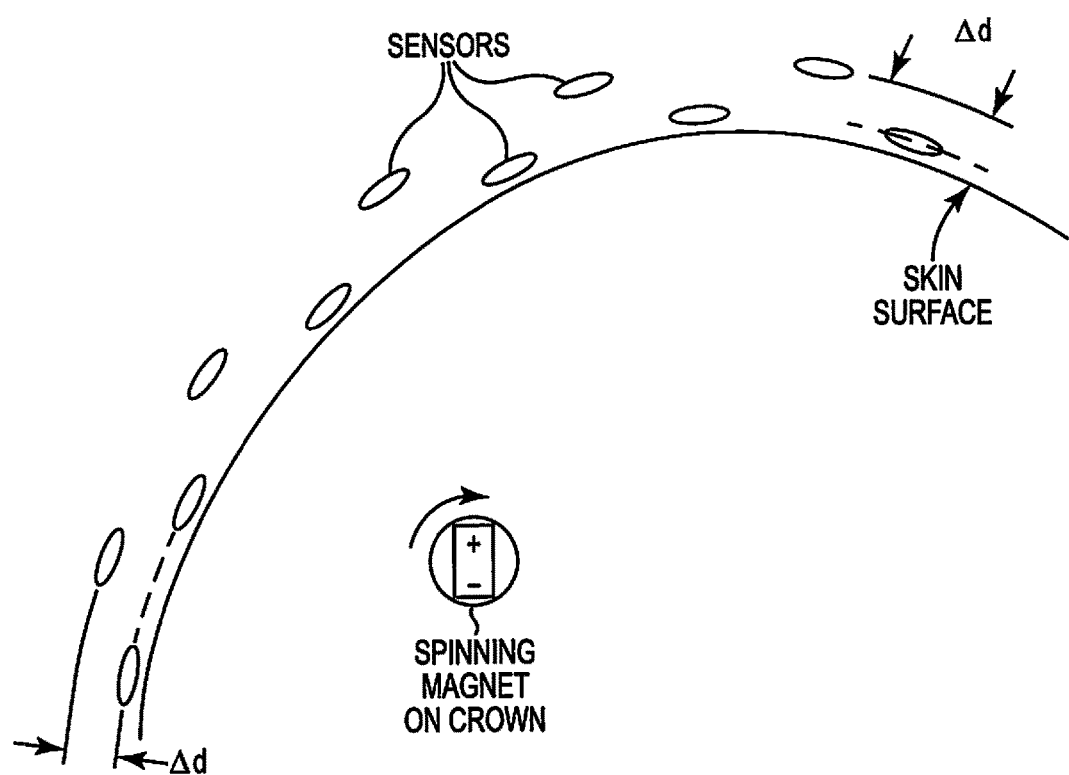
FIG. 20 illustrates one embodiment of an array of sensors outside a body and a cutaway view of one embodiment of a spinning magnet of the present invention.

It is necessary to have a rough estimate of the distance from the spinning magnet to a given sensor (y) to obtain a quantitative estimate of Ay relative to that sensor. In order to maintain high signal quality it will be desirable for the AC magnetic sensors to be as close to the spinning magnet as possible. This is either on the skin surface or as close as is reasonably possible. This means the magnet-to-sensor distance may vary from patient to patient. It means the magnet-too-sensor distance may vary from sensor to sensor on a given patient. If multiple sensors are used as described above then adjacent sensors in the array could be offset slightly in the y direction. Such small offsets between adjacent identical sensors could be used to obtain an estimate of the distance, d, from a pair of adjacent sensors in the array to the spinning magnet. FIG. 20 illustrates an array of sensors outside the body where there is a known offset between adjacent sensors.

There are four implementations which are conceptually similar. The first is the preferred implementations and the other 3 are alternative implementations.

ALTERNATIVE EMBODIMENTS

The concept of using a carrier wave as described above can be extended to other implementations. First, the emitted signal could be from one or more sources outside the body and the signal could be received by a sensor placed on or near the crown. Second, rather than using a magnetic field as the emitted signal it could be an RF field which either emanates from the crown or from one or more emitters as described above.

Alternative Embodiment #2

AC magnetic field sensor in, on or near a spinning crown which detects an AC magnetic field from one or more emitters outside the body.

Alternative Embodiment #3

A dipole embedded in, on or near the crown emits an AC signal. The emitted AC signal could be inherent to the spinning of the crown or it could emit an RF signal. One or more RF receivers located outside the body would detect the emitted signal.

Alternative Embodiment #4

Dipole embedded in, on or near the crown is used to detect an RF signal being emitted by one or more external RF emitters.

Real-Time Indication of Artery Wall Compliance, and Elastance, as the Rotational Atherectomy Procedure Progresses.

The Magnetic Carrier method and devices illustrated herein may be used to monitor the artery cross-sectional changes due to the pressure pulse changes of the heartbeat. As the exemplary vascular abrasive and/or grinding procedure progresses the measured artery cross-section evolves from something similar to a rigid pipe to a compliant tube which pulses with each heartbeat. The Magnetic Carrier method described herein can acquire information on the cross-section fast enough such that it should be possible to measure the change in artery cross-section throughout each heartbeat.

For example, a crown with an embedded magnet may spin at 2000 Hz. The heart-rate will be approximately 1 Hz. If the crown orbits or traverses the artery within the range of 5 Hz to 400 Hz it should be possible to track the size of the artery thru the course of a heartbeat. Ideally, the crown may orbit or traverse the artery dimension of interest at least 5× faster than the heart rate and at least 5× slower than the spin rate to obtain valid data for this purpose. In general, it is possible to exceed the 5× limitations with more sophisticated signal processing up to a limit of approximately 2×

Figure 21:
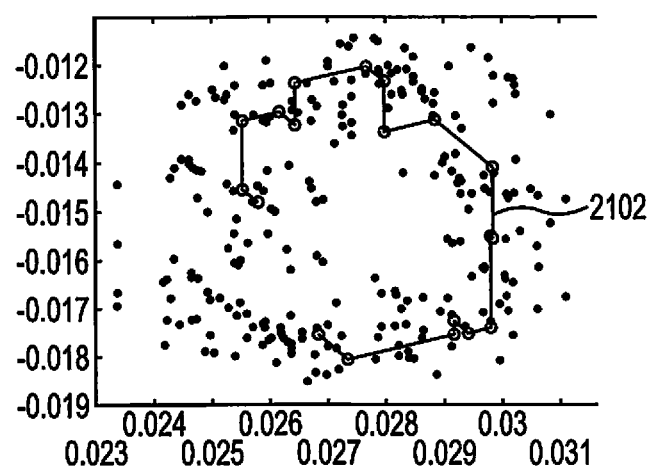
FIG. 21 illustrates positional estimates for one embodiment of the present invention.

Embodiment #1: Real-Time Monitoring of Artery Compliance During Grinding with Each Pulse of Heart A magnet is embedded in the crown. AC magnetic field sensors are arranged outside the body in a plane which is substantially perpendicular to the spin axis of the crown as described previously. FIG. 21 is an example of data obtained from an exemplary abrasive crown on a rotational atherectomy device with a magnet embedded therein and spinning in a conduit while being monitored by 3 sensors. With each rotation/spin of the crown the estimate of the crown's position is updated 3 times, once for each sensor. The data points in FIG. 21 represent estimates of the crown's position. The connected data points 2102 are the position estimates from the most recent 7 revolutions/rotations/spins of the crown used to generate the data. This example illustrates the crown has not quite completed an orbit of the conduit, e.g., blood vessel in 7 rotational revolutions. It is also apparent that the dimensions of the artery could be estimated as often as each orbit. The values on the axes of the graph are raw data from the magnetic sensor and have not been converted to units of length.

Embodiment #2: Real-Time Monitoring of Artery Compliance with Each Pulse of Heart with Minimal Grinding The crown surface morphology is designed such that it will grind when spinning in one direction and do minimal grinding when spinning in the opposite direction. In this manner the crown can be used to monitor artery compliance changes either during the grinding process or, by spinning in the opposite direction, the artery compliance with minimal grinding.

The operating theory underlying the Magnetic Carrier (MC) concept is described supra but one means of representing the concept is with the following equation:

$$\frac{\Delta x}{x} = -\frac{1}{2} \cdot \frac{\Delta B}{B}. \quad \text{EQ 1}$$

Where:

X is the distance from sensor to spinning crown;

Δx is a minor change or variation in x which is movement of the crown relative to the sensor;

B is the peak to peak signal strength of the sensed magnetic carrier wave; and

ΔB is the minor change or variation in B.

Signal Integration Mitigates Effect of Crown Oscillation

Why Crown Oscillation is a Problem

Eq #1 is similar to F=m*A in that it is a simple expression of the relationship between physical parameters of a system which can be applied and interpreted in a variety of ways.

For example, it is assumed that the signal from a magnetic sensor is linearly proportional to the strength of the magnetic field, B, and therefore the sensor voltage is interchangeable with B in the formula.

While there are many types of magnetic field sensors which could be used, the MC sensors used in the following examples are inductive pickup coils which provide a signal strength which is proportional to the rate of change of the magnetic field, dB/dt or $\dot{B}$. If the speed of crown rotation is relatively constant over a sufficiently long period of time then the ratios based on magnetic field strength, ΔB/B and rate of change of magnetic field strength, $\Delta\dot{B}/\dot{B}$, are essentially interchangeable.

Figure 22:
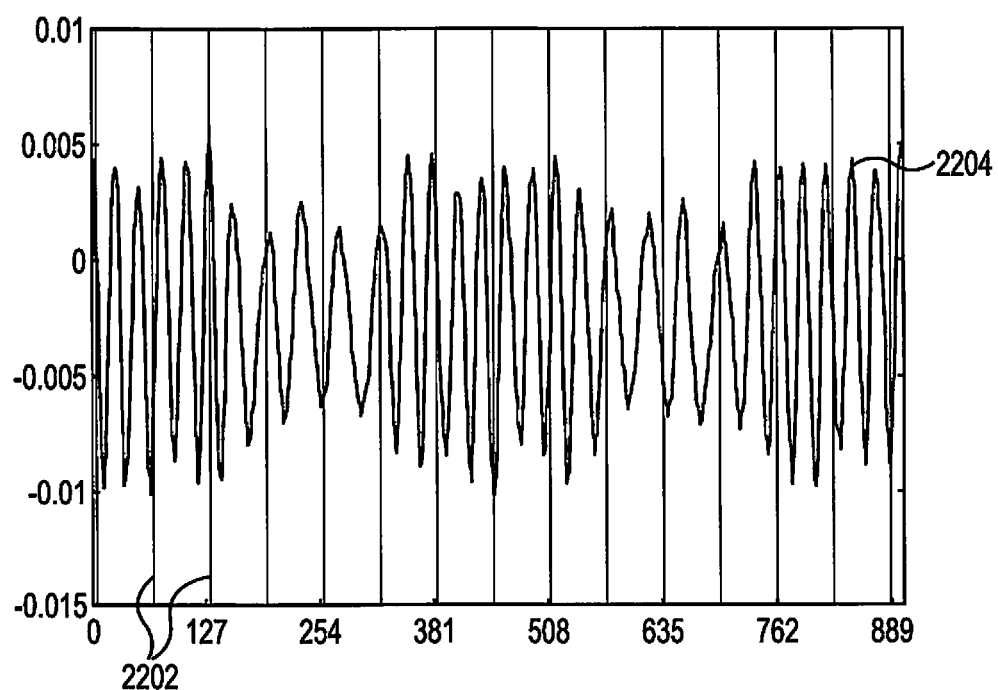
FIG. 22 illustrates revolutions of one embodiment of the present invention.

However, the crown speed is not necessarily constant over a sufficiently long period of time. Thus, FIG. 22 illustrates how severe the crown oscillation may become in a device which has been used excessively. The vertical 2202 lines are from the motor hall sensor which confirm the motor speed is constant. Line 2204 is the signal obtained from inductive pickup coils. Each cycle of the line 2204 represents a revolution of the crown during rotation with a rotational atherectomy device. The crown periodically slows down as indicated by the periods when the line 2204 widens out. When the crown slows down the peak to peak signal strength also reduces. When the crown speeds back up the peak to peak signal strength also increases. Therefore, the oscillation of crown speed modulates the signal strength of the carrier wave.

Given that the Magnetic Carrier concept relies on variation of signal strength due to orbit within the artery lumen, the modulation of signal strength due to oscillation of the crown is a potentially severe noise source.

Mitigation of the Effect of Crown Oscillation.

While crown oscillation introduces noise for a rate of change of magnetic field sensor it will not introduce noise for a magnetic field sensor.

The inductive sensor output is linearly proportional to the rate of change of the magnetic field which means its signal is linearly proportional to the derivative of the signal from a magnetic field sensor. Therefore, by taking an appropriate s-domain transform of the signal from the inductive coil sensor creates a virtual magnetic field sensor which is largely immune to crown oscillation.

An example of one method to implement an appropriate s-domain transform.

The integration of the signal from the inductive coil sensor can be accomplished in software on a point by point basis as follows:

If $X_i$ is a signal data point acquired from the inductive coil sensor then an appropriate s-domain transform can be sufficiently approximated by taking the cumulative sum of the incoming signal such as follows:

$$X\_cumsum_i = X\_cumsum_{i-1} + X_i$$

If the incoming signal has even a small offset this cumulative sum calculation can quickly become a large positive or negative number. Therefore it may be desirable to apply a high-pass filter before and/or after the cumulative sum calculation where the cutoff frequency is well below the spin and orbit frequencies of the crown.

There are many possible transforms which could be applied to the acquired signal to mitigate crown oscillation. It is likely there is an transform which would be more effective than a cumulative sum, which the skilled artisan will readily recognize. The combination of a cumulative sum and high pass filter is simply provided as an example which can be easily applied.

Example of Signal Integration Applied to
Bench-Test Data

Figure 23:
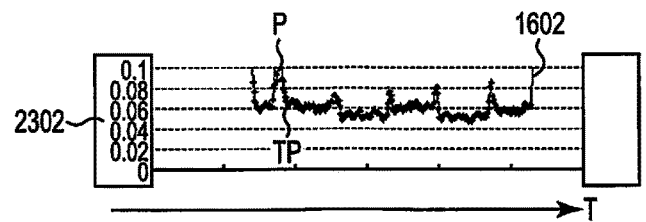
FIG. 23 illustrates one embodiment of the present invention for estimating lumen diameter.
Figure 24:
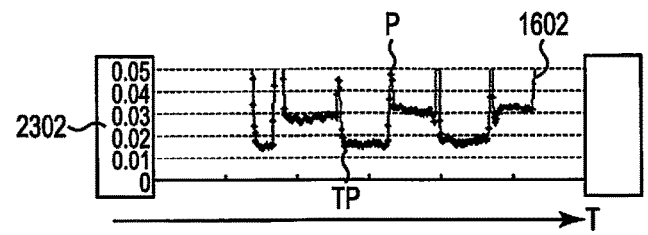
FIG. 24 illustrates one embodiment of the present invention for estimating lumen diameter.

Graphs shown in FIGS. 23 and 24 are carrier wave 1602 results from a bench-top test (20150105R007) where spinning crown with embedded magnet(s) is moved back and forth between large (ID=4.02 mm) and small (ID=2.78 mm) tubing every few seconds.

Both graphs have a common x-axis which is time in seconds T. The entire graph window is 30 seconds in both cases.

Y-axis is unsealed estimate of tubing ID 2302 from a single rate of change of magnetic field sensor which is 3" away from the spinning crown with magnet(s).

Results in both graphs are based on the same data set. The only difference in the results shown is the data-processing method used.

The graph of FIG. 23 shows unsealed results of carrier wave 1602 based on one embodiment of a method of estimating lumen diameter seen as the average peak P to trough Tr distance. The change in lumen size estimate as the magnetic carrier crown moves between the large and small ID tubing is barely discernable.

S-Domain Transform Signal to Make Results Immune to Oscillation of Crown

Unsealed results shown in FIG. 24 use the cumulative sum of the integrated signal with the original method of estimating lumen diameter. The cumulative sum removes the noise due to the crown oscillating while the crown spins. Referring to FIG. 24, it is much more evident when the crown moves back and forth between the large and small diameter sections of conduit constraining the crown's orbit.

Further Refinement: Chord Method Extracts Crown Orbit from Movement Artifact

Spinning magnetic Crown emits a carrier wave (1 cycle/spin);

The carrier wave magnitude modulates as the crown orbits closer to or further from sensor; and The carrier wave modulation over many orbits is used to estimate lumen diameter.

Gross movement (such as in coronary arteries due to heart beat) causes additional variation in carrier wave signal magnitude which can significantly bias the lumen diameter estimate obtained from the Original Method.

Chord Method with One Sensor:

On every spin the chord projections to recent spin locations are calculated. (See attached PowerPoint). Because chord projections are based on recent spin locations such as within the previous 20 ms, there is insufficient time for gross movement to have a significant impact; and The chord projections obtained over a sufficiently long period of time (such as 0.5 s) can then be used to provide a precise estimate of lumen size which is largely free of movement artifact.

Chord Method with Two or More Non-Aligned Sensors:

On every spin the chord projections to recent spin locations are calculated for each sensor.

The chord projections from 2 or more non-aligned sensors are used to estimate the actual chord lengths.

The chord lengths obtained over a sufficiently long period of time (such as 0.5 s) can then be used to estimate lumen size.

Two or more non-aligned sensors should provide an estimate which is dramatically more powerful than can be obtained from a single sensor.

If three or more non-aligned sensors are used it is possible to make a near-real-time error estimate of each chord length. This has potential for use as a double-check that valid data is being acquired, to select the sensor subset providing the most valid data.

Working Example of Chord Method Applied to
Animal Study Data

Figure 25:
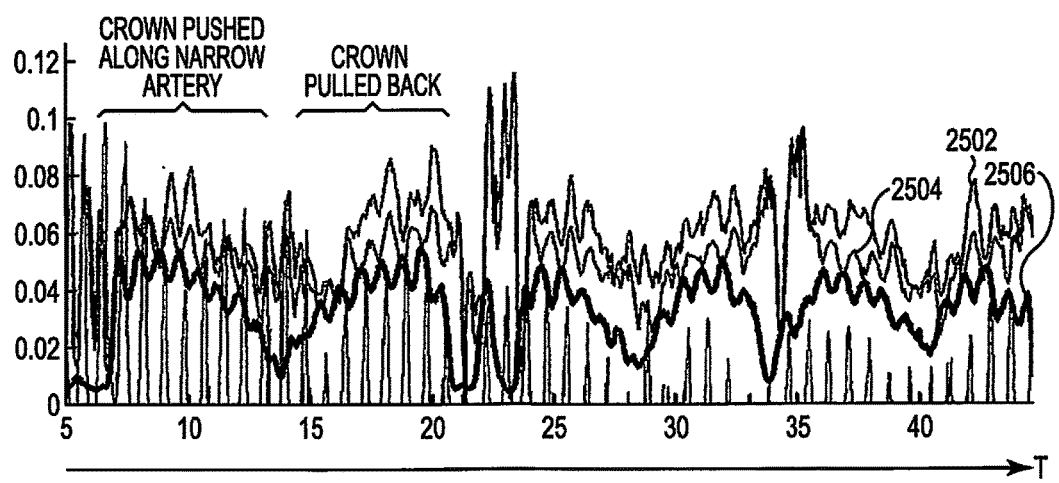
FIG. 25 illustrates one embodiment of the present invention for estimating lumen diameter under varying conditions.

The graphical data of FIG. 25 are from animal study data taken in the femoral artery of a live pig with a 2.25 mm MC crown.

Description of Graph:

The x-axis in the graph below is time in seconds.

The y-axis is unsealed lumen diameter of the internal femoral artery of a swine.

The relatively noisy trace 2502 is the Original Calculation method used in FIG. 23.

The less noisy trace 2504 is the Original Calculation method but also using a cumulatively summed signal.

The much less noisy black trace 2506 is the Chord-based method using a cumulatively summed signal.

The pulsing of the artery can be seen to coincide with the blood pressure trace (with a slight calculation offset, depending on the method applied).

Experimental technique: The spinning crown was pushed along the narrowing artery, then retracted as indicated on the graph below. This process was repeated two more times.

Working Example of Chord Method Applied to
Bench-Top Data

The following data are from bench-top testing.

Figure 26:
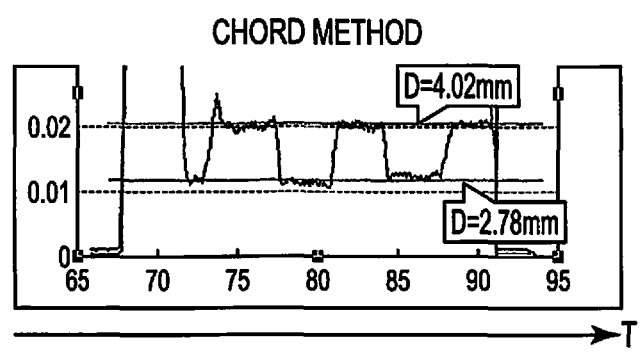
FIG. 26 illustrates one embodiment of the present invention for estimating lumen diameter.

Graphs in FIGS. 23, 24 and 26 are results from a bench-top test (20150105R007) where spinning MC Crown is moved back and forth between large (ID=4.02 mm) and small (ID=2.78 mm) tubing every few seconds.

All graphs of FIGS. 23, 24 and 26 have a common x-axis which is time in seconds. The entire graph window is 30 seconds.

Y-axis is unsealed estimate of tubing ID from a single rate of change of magnetic field sensor which is 3" away from the spinning crown.

Results in all graphs are based on the same data set. The only difference in the results shown is the data-processing method used.

The graph FIG. 23 shows unsealed results based on the original MC calculation method. The change in signal as the MC crown moves between the large and small ID tubing is barely discernable.

Cumulative Sum the Signal to Make Results Immune to Crown Method:

Unsealed results in the graph of FIG. 24 use a cumulative sum signal with the original calculation method. Cumulative sum removes the noise due to the crown oscillating while it spins. It is much more evident when the crown moves back and forth between the two diameters.

Chord-Based Method:

Unsealed results in the graph of FIG. 26 use a cumulative sum signal with the Chord-based calculation method. The chord-based method separates crown orbit (artery lumen size) from gross movement such as heart movement/twisting.

In the case where there is no gross movement the Chord Based method has a minor but noticeable benefit over the Original Method.

Opposed Configuration of Sensors to Mitigate Effects of Gross Movement.

The Opposed Configuration of MC Sensors is intended to mitigate the artifact introduced by gross movement of the heart.

The far-field magnetic strength to distance relationship has been previously disclosed and is described in equations (1) and (2) below for MC sensors #1 and #2, respectively. The two sensors are substantially aligned but on opposite sides of the spinning/orbiting crown which is why it is called the "Opposed Configuration".

Movement artifact biases the lumen estimate in at least two ways:

As shown in FIG. 27, the distance between sensor to spinning crown, $x_1$ and $x_2$, will change slightly with heart movement which will create a small oscillating offset in the lumen estimate.

The heart movement artifact will introduce additional unwanted variation in Ax for the Original Method which is largely suppressed with the Chord Method.

The heart movement artifact can be removed algebraically with the opposed configuration and the result is described in equation #5 in FIG. 27. Note, in particular, the distances, x1 and x2, from the spinning crown to each of the two sensors, S1 and S2, no longer appears in equation #5. The only geometric input required in equation #5 is xT which is the distance between the two sensors in the opposed configuration. As long as the two sensors do not move relative to each other the result of equation #5 will be largely immune to gross movement of the heart. An additional outcome of separating lumen size from gross movement is that it is also possible to estimate the gross movement as described in equation #6 of FIG. 27.

The combination of having 2 MC sensors in an Opposed Configuration and applying the Chord Method thus effectively mitigates movement artifact in the lumen estimate.

Working Example of Opposed Configuration Applied to Animal Study Data

Figure 28:
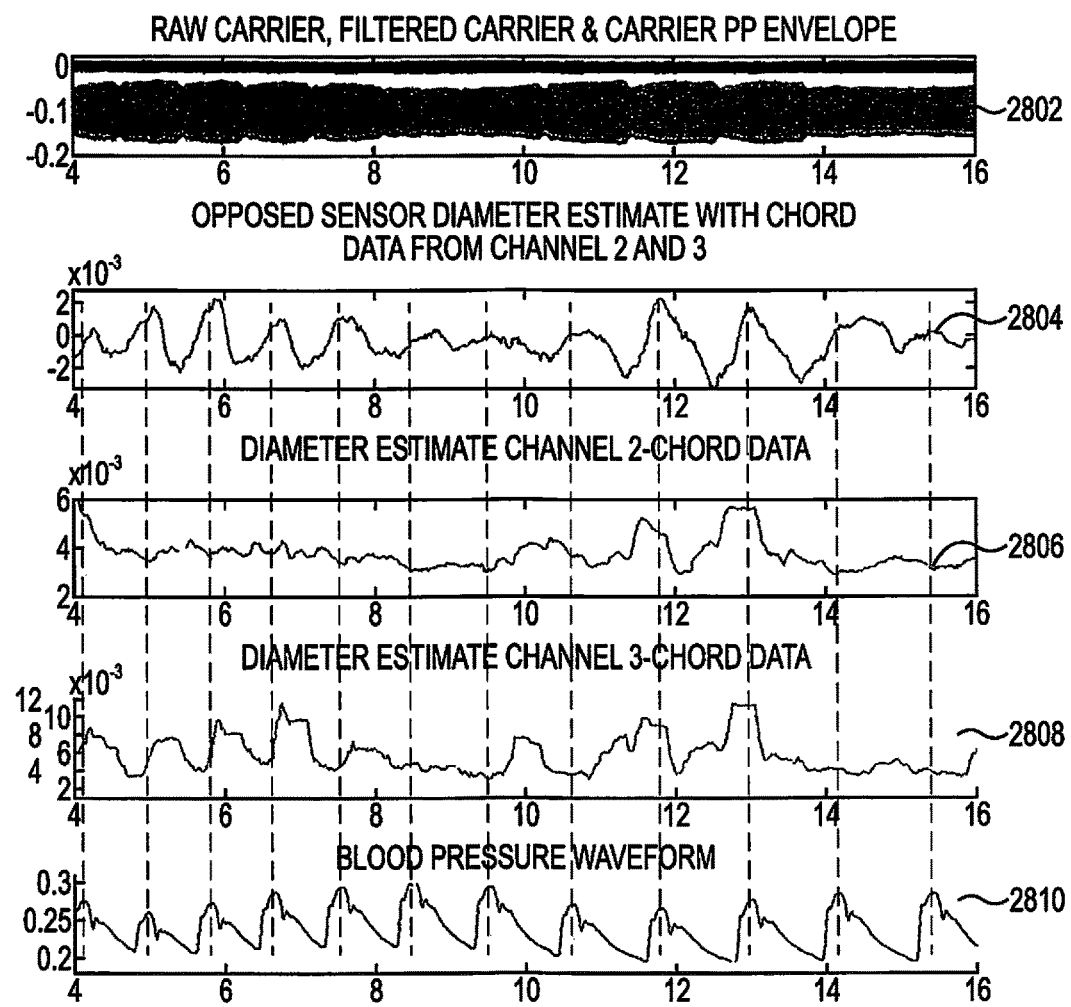
FIG. 28 illustrates several embodiments of the present invention for estimating lumen diameter.

Description of Graphical Results illustrated in FIG. 28:
The data is from the animal study conducted on live pigs.
The x-axis is time in seconds.
The top subplot is raw signal magnitude 2802.
The second subplot trace is the Opposed Lumen Estimate 2804.
The third & fourth subplot's traces are the Chord-based estimates from each individual sensor 2806, 2808, using 2 and 3 chords respectively.
The fourth subplot trace is the heart pressure trace 2810.

Conclusions: The second subplot trace of Opposed Configuration lumen estimate 2804 is noticeably more well-behaved and yields the expected result as compared to the third and fourth subplot traces 2806, 2808 based on the individual sensors. Note that dashed vertical lines have been added to the figure to assist visual alignment of the blood pressure trace with the lumen size estimates.

The following information or data may be extracted using the above-described magnetic carrier wave methods, devices and systems:

1. Diameter of lumen of conduit or exemplary blood vessel.

2. Cross-sectional shaping of the lumen of conduit or exemplary blood vessel.

3. Low frequency signature sound of exemplary abrasive element in a rotational atherectomy system impacting the wall of exemplary blood vessel.

4. High frequency signature of crown impacting the wall of exemplary blood vessel.

5. Oscillation and angular deflection of exemplary abrasive element, e.g., a crown or burr in a rotational atherectomy system. Oscillatory behavior of the rotating abrasive element assists in evaluating and assessing the composition of the exemplary blood vessel and/or lesion therein.

As described above, the methods, devices and systems of the magnetic carrier wave embodiments may be made progressively more accurate by, inter alia, removing interfering noise. From least accurate, or most noisy, to most accurate, or least noisy, these methods, devices and systems comprise at least the following:

1. The initial magnetic carrier wave method comprising at least one magnetic sensor;

2. Integration of signal with the initial magnetic carrier wave method;

3. Chord method and comprising one sensor, without no. 2's integration step;

4. Chord method and comprising one magnetic sensor and with integration of signal with the initial magnetic carrier wave method;

5. Chord method and comprising two magnetic sensors not in opposition, thus beginning to mitigate gross movement effects;

6. Chord method and comprising two, or more, magnetic sensors in opposition to each other;

7. Chord method and comprising three or more magnetic sensors, none of the sensors in opposition; and 8. Chord method and comprising three or more magnetic sensors, with at least two of the three or more sensors in opposition.

Various embodiments of the present invention may be incorporated into a rotational atherectomy system as described generally in U.S. Pat. No. 6,494,890, entitled "ECCENTRIC ROTATIONAL ATHERECTOMY DEVICE," which is incorporated herein by reference. Additionally, the disclosure of the following co-owned patents or patent applications are herein incorporated by reference in their entireties: U.S. Pat. No. 6,295,712, entitled "ROTATIONAL ATHERECTOMY DEVICE"; U.S. Pat. No. 6,132,444, entitled "ECCENTRIC DRIVE SHAFT FOR ATHERECTOMY DEVICE AND METHOD FOR MANUFACTURE"; U.S. Pat. No. 6,638,288, entitled "ECCENTRIC DRIVE SHAFT FOR ATHERECTOMY DEVICE AND METHOD FOR MANUFACTURE"; U.S. Pat. No. 5,314,438, entitled "ABRASIVE DRIVE SHAFT DEVICE FOR ROTATIONAL ATHERECTOMY"; U.S. Pat. No. 6,217,595, entitled "ROTATIONAL ATHERECTOMY DEVICE"; U.S. Pat. No. 5,554,163, entitled "ATHEREC- TOMY DEVICE"; U.S. Pat. No. 7,507,245, entitled "ROTATIONAL ANGIOPLASTY DEVICE WITH ABRASIVE CROWN"; U.S. Pat. No. 6,129,734, entitled "ROTATIONAL ATHERECTOMY DEVICE WITH RADIALLY EXPANDABLE PRIME MOVER COUPLING"; U.S. Pat. No. 8,597,313, entitled "ECCENTRIC ABRADING HEAD FOR HIGH-SPEED ROTATIONAL ATHERECTOMY DEVICES"; U.S. Pat. No. 8,439,937, entitled "SYSTEM, APPARATUS AND METHOD FOR OPENING AN OCCLUDED LESION"; U.S. Pat. Pub. No. 2009/0299392, entitled "ECCENTRIC ABRADING ELEMENT FOR HIGH-SPEED ROTATIONAL ATHERECTOMY DEVICES"; U.S. Pat. Pub. No. 2010/0198239, entitled "MULTI-MATERIAL ABRADING HEAD FOR ATHERECTOMY DEVICES HAVING LATERALLY DISPLACED CENTER OF MASS"; U.S. Pat. Pub. No. 2010/0036402, entitled "ROTATIONAL ATHERECTOMY DEVICE WITH PRE-CURVED DRIVE SHAFT"; U.S. Pat. Pub. No. 2009/0299391, entitled "ECCENTRIC ABRADING AND CUTTING HEAD FOR HIGH-SPEED ROTATIONAL ATHERECTOMY DEVICES"; U.S. Pat. Pub. No. 2010/0100110, entitled "ECCENTRIC ABRADING AND CUTTING HEAD FOR HIGH-SPEED ROTATIONAL ATHERECTOMY DEVICES"; U.S. Design Pat. No. D610258, entitled "ROTATIONAL ATHERECTOMY ABRASIVE CROWN"; U.S. Design Pat. No. D6107102, entitled "ROTATIONAL ATHERECTOMY ABRASIVE CROWN"; U.S. Pat. Pub. No. 2009/0306689, entitled "BIDIRECTIONAL EXPANDABLE HEAD FOR ROTATIONAL ATHERECTOMY DEVICE"; U.S. Pat. Pub. No. 2010/0211088, entitled "ROTATIONAL ATHERECTOMY SEGMENTED ABRADING HEAD AND METHOD TO IMPROVE ABRADING EFFICIENCY"; U.S. Pat. Pub. No. 2013/0018398, entitled "ROTATIONAL ATHERECTOMY DEVICE WITH ELECTRIC MOTOR"; and U.S. Pat. No. 7,666,202, entitled "ORBITAL ATHERECTOMY DEVICE GUIDE WIRE DESIGN." It is contemplated by this invention that the features of one or more of the embodiments of the present invention may be combined with one or more features of the embodiments of atherectomy devices described therein.

The present invention should not be considered limited to the particular examples described above, but rather should be understood to cover all aspects of the invention. Various modifications, equivalent processes, as well as numerous structures to which the present invention may be applicable will be readily apparent to those of skill in the art to which the present invention is directed upon review of the present specification.

What is claimed is:

1. A method for assessing characteristics of a blood vessel in a patient during a rotational medical procedure performed within the blood vessel, comprising:
   providing a rotational medical system comprising a rotational drive shaft and a prime mover adapted to rotate the rotational drive shaft;
   providing at least one magnet, wherein the at least one magnet is located within the blood vessel and adapted to rotate when the rotational drive shaft rotates;
   providing at least one magnetic field sensor;
   generating a magnetic field by rotating the rotational drive shaft and the at least one magnet;
   sensing with the at least one magnetic field sensor, the location of the at least one magnet as it rotates and obtaining a first set of test data;
   determining, with the sensed location of the at least one magnet, at least one of the following characteristics of the blood vessel within the group consisting of: the diameter of the blood vessel, the cross-sectional shape of the blood vessel, the cross-sectional shape of an occlusion within the blood vessel, the compliance of the blood vessel, the elastance of the blood vessel, whether the blood vessel is at least partially calcified, the relative amount of calcification, the frequency with which the at least one magnet impacts the wall of the blood vessel.

2. The method of claim 1, further comprising obtaining a second set of test data, and comparing the second set of test data to the first set of test data.

3. The method of claim 2, further comprising obtaining at least one set of reference data and comparing the second set of test data to the at least one set of reference data.

4. The method of claim 2, further comprising monitoring the progress of the rotational medical procedure in real time.

5. The method of claim 2, further comprising using the obtained sets of test data to assess the completeness of the rotational medical procedure.

6. The method of claim 2, wherein the rotational drive shaft comprises at least one abrasive element, wherein the at least one magnet is located on, in or near the at least one abrasive element.

7. The method of claim 1, further comprising obtaining at least one set of reference data and comparing the first set of test data to the at least one set of reference data.

8. The method of claim 1, wherein the rotational medical procedure comprises rotational atherectomy and the rotational medical system comprises a rotational atherectomy system.

9. A method for assessing characteristics of a blood vessel in a patient during a rotational medical procedure performed within the blood vessel, comprising:
   providing a rotational medical system comprising a rotational drive shaft and a prime mover adapted to rotate the rotational drive shaft;
   providing at least one field emitter, wherein the at least one field emitter is located within the blood vessel and adapted to rotate when the rotational drive shaft rotates;
   providing at least one field emitter sensor located external to the patient;
   generating an emitted field by rotating the rotational drive shaft and the at least one magnet;
   sensing with the at least one field sensor, the location of the at least one field emitter as it rotates and obtaining a first set of test data;
   determining, with the sensed location of the at least one field emitter, at least one of the following characteristics of the blood vessel within the group consisting of: the diameter of the blood vessel, the cross-sectional shape of the blood vessel, the cross-sectional shape of an occlusion within the blood vessel, the compliance of the blood vessel, the elastance of the blood vessel, whether the blood vessel is at least partially calcified, the relative amount of calcification, the frequency with which the at least one field emitter impacts the wall of the blood vessel.

10. The method of claim 9, wherein the at least one field emitter comprises a radiofrequency (RF) emitter and the at least one field sensor comprises an RF sensor.

11. The method of claim 10, further comprising obtaining a second set of test data, and comparing the second set of test data to the first set of test data.

12. The method of claim 11, further comprising obtaining at least one set of reference data and comparing the second set of test data to the at least one set of reference data.

13. The method of claim 11, further comprising monitoring the progress of the rotational medical procedure in real time.

14. The method of claim 9, further comprising obtaining at least one set of reference data and comparing the first set of test data to the at least one set of reference data.

15. The method of claim 14, further comprising using the obtained sets of test data to assess the completeness of the rotational medical procedure.

16. The method of claim 15, wherein the rotational medical procedure comprises rotational atherectomy and the rotational medical system comprises a rotational atherectomy system.

17. The method of claim 16, wherein the rotational drive shaft comprises at least one abrasive element, wherein the at least one RF field emitter is located on, in or near the at least one abrasive element.

* * * * *